United States Patent
Natsumeda et al.

(10) Patent No.: US 9,028,071 B2
(45) Date of Patent: May 12, 2015

(54) LIGHT EMITTING ELEMENT, LIGHT SOURCE DEVICE, AND PROJECTION DISPLAY DEVICE

(75) Inventors: Masanao Natsumeda, Minato-ku (JP); Shin Tominaga, Minato-ku (JP); Goroh Saitoh, Minato-ku (JP); Masao Imai, Minato-ku (JP)

(73) Assignee: NEC Corporation, Tokyo (JP)

( * ) Notice: Subject to any disclaimer, the term of this patent is extended or adjusted under 35 U.S.C. 154(b) by 429 days.

(21) Appl. No.: 13/504,863

(22) PCT Filed: Oct. 14, 2010

(86) PCT No.: PCT/JP2010/068014
§ 371 (c)(1),
(2), (4) Date: Apr. 27, 2012

(87) PCT Pub. No.: WO2011/052387
PCT Pub. Date: May 5, 2011

(65) Prior Publication Data
US 2012/0224148 A1    Sep. 6, 2012

(30) Foreign Application Priority Data

Oct. 30, 2009    (JP) .................................. 2009-250282

(51) Int. Cl.
*G03B 21/14*    (2006.01)
*H01L 33/00*    (2010.01)
(Continued)

(52) U.S. Cl.
CPC ................ *G02B 5/008* (2013.01); *G02B 6/005* (2013.01); *G02B 26/02* (2013.01); *G02B 6/1226* (2013.01);
(Continued)

(58) Field of Classification Search
CPC ........ G03B 21/00; G03B 21/14; G02B 5/008; G02B 6/005; G02B 26/02; G02B 6/1226; H01L 51/5262; G01N 21/553; G01N 21/648; G02F 1/133606; H04N 9/3152

USPC .................................. 353/20, 30, 97; 257/98
See application file for complete search history.

(56) References Cited

U.S. PATENT DOCUMENTS

| 2006/0278888 A1 | 12/2006 | Kim et al. | |
|---|---|---|---|
| 2007/0181889 A1* | 8/2007 | Orita | 257/79 |
| 2012/0176766 A1* | 7/2012 | Natsumeda | 362/19 |

FOREIGN PATENT DOCUMENTS

| CN | 100426535 C | 10/2008 |
|---|---|---|
| JP | 2005-005679 A | 1/2005 |

(Continued)

OTHER PUBLICATIONS

"PhlatLight™ Photonic Lattice LEDs for RPTV Light Engines" Christian Hoapfner, SID Symposium Digest 37, 2006, p. 1808.
(Continued)

*Primary Examiner* — Toan Ton
*Assistant Examiner* — Magda Cruz
(74) *Attorney, Agent, or Firm* — Sughrue Mion, PLLC

(57) ABSTRACT

Light source layer (4) includes substrate (10) and a pair of layers, namely, hole-transport layer (11) and electron-transport layer (13), formed on substrate (10). Directional control layer (5) includes plasmon excitation layer (15) stacked on a side of light source layer (4), which is opposite to the side of substrate (10) of light source layer (4), and which has a plasma frequency higher than a frequency of light output from light source layer (4), and wave vector conversion layer (17) stacked on plasmon excitation layer (15), which converts light incident from plasmon excitation layer (15) into light having a predetermined exit angle to output the light. Plasmon excitation layer (15) is sandwiched between low dielectric constant layer (14) and high dielectric constant layer (16).

26 Claims, 19 Drawing Sheets

(51) Int. Cl.
  *G02B 5/00* (2006.01)
  *F21V 8/00* (2006.01)
  *G02B 26/02* (2006.01)
  *G02B 6/122* (2006.01)
  *G01N 21/552* (2014.01)
  *G01N 21/64* (2006.01)
  *G02F 1/1335* (2006.01)
  *H04N 9/31* (2006.01)
  *G02B 3/00* (2006.01)
  *G02B 5/30* (2006.01)
  *H01L 51/52* (2006.01)

(52) U.S. Cl.
  CPC ............ *G01N 21/553* (2013.01); *G01N 21/648* (2013.01); *G02F 1/133606* (2013.01); *H04N 9/3152* (2013.01); *G02B 3/0031* (2013.01); *G02B 5/3016* (2013.01); *G03B 21/14* (2013.01); *H01L 51/5262* (2013.01); *H01L 51/5275* (2013.01); *H01L 2933/0083* (2013.01)

(56) References Cited

FOREIGN PATENT DOCUMENTS

| | | |
|---|---|---|
| JP | 2006-313667 A | 11/2006 |
| JP | 2006-339627 A | 12/2006 |
| JP | 2007-214260 A | 8/2007 |
| WO | 2007/038070 A1 | 4/2007 |

OTHER PUBLICATIONS

Office Action dated Apr. 9, 2014, issued by the State Intellectual Property Office of the P.R.C. in corresponding Chinese Application No. 201080049200.6.

Wang et al., "Progress of Beam Control Based on Metal Surface Plasmon Polaritons", Optical Technique, vol. 35, No. 2, pp. 163 to 174, Mar. 31, 2009.

* cited by examiner ated Oct. 14, 2010, claiming
LIGHT EMITTING ELEMENT, LIGHT SOURCE DEVICE, AND PROJECTION DISPLAY DEVICE

CROSS REFERENCE TO RELATED APPLICATIONS

This application is a National Stage of International Application No. PCT/JP2010/068014 filed Oct. 14, 2010, claiming priority based on Japanese Patent Application No. 2009-250282 filed Oct. 30, 2009, the contents of all of which are incorporated herein by reference in their entirety.

TECHNICAL FIELD

The present invention relates to a light emitting element that uses plasmon coupling to output light, a light source device, and a projection display device.

BACKGROUND ART

There has been proposed a LED (light-emitting diode) projector that uses a LED as a light emitting element of a light source. The LED projector of this type includes an illumination optical system into which light from the LED enters, a light bulb having a liquid crystal display plate or a DMD (Digital Micromirror Device) into which light from the illumination optical system enters, and a projection optical system for projecting light from the light bulb to a projection surface.

In the LED projector, to increase the luminance of a projected image, light loss must be prevented as much as possible on an optical path from the LED to the light bulb.

As described in Nonpatent Literature 1, there are restrictions based on etendue that are determined by the product of an area of the light source and the radiation angle. In other words, the light from the light source is not used as projection light unless a value of the product of the light-emitting area of the light source and the radiation angle is set equal to or less than a value of the product of an incident surface area of the light bulb and a capture angle (solid angle) determined by the F number of the illumination optical system.

Thus, reducing light loss by lowering the etendue of light output from the LED is an issue that requires attention.

In the light source of the LED projector, a light source to emit a luminous flux of about several thousand lumina is required. To achieve this, a LED having high luminance and high directionality is essential.

As an example of such a light emitting element having high luminance and high directionality, as shown in FIG. 1, Patent Literature 1 discloses a semiconductor light emitting element configured by sequentially stacking n-type GaN layer 102, InGaN active layer 103, p-type GaN layer 104, ITO transparent electrode layer 105, and two-dimensional periodic structure layer 109 on sapphire substrate 101. This light emitting element, a part of which is cut out to form groove 108, includes n-side bonding electrode 106 disposed in a part of n-type GaN layer 102 in groove 108, and p-side bonding electrode 107 disposed in ITO transparent electrode layer 105. In this light emitting element, directionality of light from InGaN active layer 103 is increased by two-dimensional periodic structure layer 109. Then, the light is output from the light emitting element.

As another example of the light emitting element having high luminance and high directionality, as shown in FIG. 2, Patent Literature 2 discloses organic EL element 110 configured by stacking anode layer 112, hole-transport layer 113, light emitting layer 114, electron-transport layer 115, and cathode layer 116 having micro periodic relief structure grating 116a on substrate 111. This light emitting element has high directionality that enables setting of a radiation angle of light output from the light emitting element to be less than ±15° due to the effect of surface plasmons propagated through an interface between micro periodic relief structure grating 116a of cathode layer 116 and the outside.

CITATION LIST

Patent Literature

Patent Literature 1: JP2005-005679A
Patent Literature 2: JP2006-313667A

Nonpatent Literature

Nonpatent Literature 1: PhlatLight™ Photonic Lattice LEDs for RPTV Light Engines Christian Hoepiher, SID Symposium Digest 37, 1808 (2006)

SUMMARY OF INVENTION

As described above, in the LED projector, light output from the light emitting element at a fixed angle (e.g., radiation angle of ±15°) is lost without having entered to the illumination optical system or the light bulb. In the configuration described in Patent Literature 1, an LED that radiates a luminous flux of about several thousand lumina is currently provided, achieving high luminance. However, the radiation angle of the output light cannot be set less than ±15°. In other words, the light emitting element described in Patent Literature 1 has a problem of low directionality of the output light.

On the other hand, in the configuration described in Patent Literature 2, use of the surface plasmons enables setting of the radiation angle of the output light to be less than ±15°. Currently, however, there is no organic EL element that radiates a luminous flux of about several thousand lumina, and hence sufficient luminance cannot be acquired even when the light emitting element described in Patent Literature 2 is applied to the LED projector.

In other words, the configurations disclosed in Patent Literatures 1 and 2 cannot achieve a light emitting element that has both luminance and directionality necessary for the LED projector.

It is an object of the present invention to provide a light emitting element that can solve the abovementioned problems of the related technologies, and a light source device and a projection display device that include the same.

Solution to Problems

To achieve the object, a light emitting element according to the present invention includes a light source layer and an optical element layer stacked on the light source layer, into which light from the light source layer enters. The light source layer includes a substrate and a pair of layers, namely, a hole-transport layer and an electron-transport layer, formed on the substrate. The optical element layer includes a plasmon excitation layer stacked on a side opposite the substrate side of the light source layer, which has a plasma frequency higher than a frequency of light output from the light source layer, and an exit layer stacked on the plasmon excitation layer, which converts light incident from the plasmon excitation layer into light having a predetermined exit angle to output the light. The plasmon excitation layer is sandwiched between two layers having dielectric properties.

A light source device according to the present invention includes the light emitting element of the present invention, and a polarizing conversion element that sets axially symmetric polarized light incident from the light emitting element in a predetermined polarized state.

A projection display device according to the present invention includes the light emitting element of the present invention, a display element that adds image information to the light output from the light emitting element, and a projection optical system that projects a projected image by light output from the display element.

Effects of Invention

According to the present invention, luminance and directionality of the output light can be simultaneously increased. As a result, a light emitting element having high luminance and high directionality can be achieved.

DESCRIPTION OF EMBODIMENTS

Next, specific embodiments of the present invention are described with reference to the accompanying drawings.

First Embodiment

Figure 1:
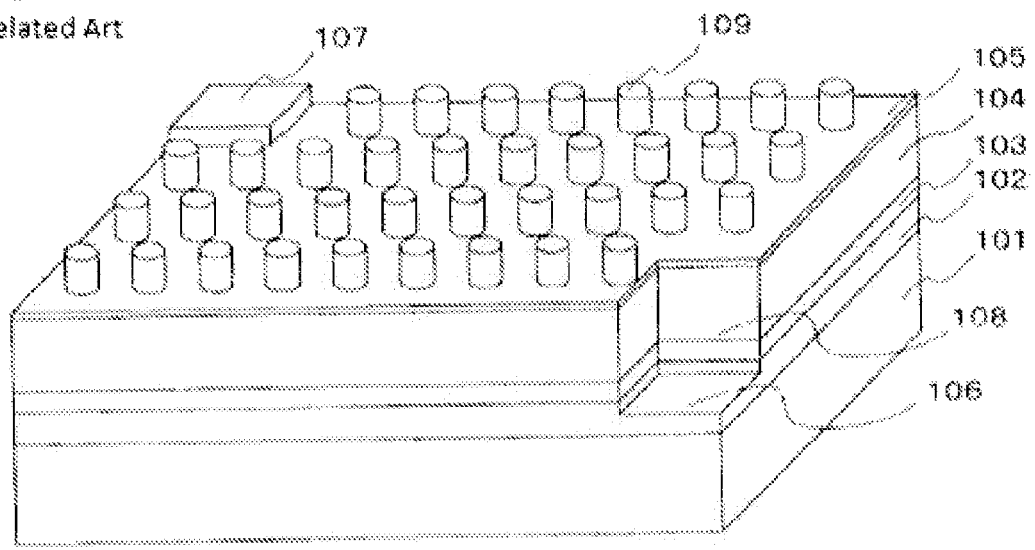
FIG. 1 is an explanatory perspective view showing a configuration according to Patent Literature 1.
Figure 2:
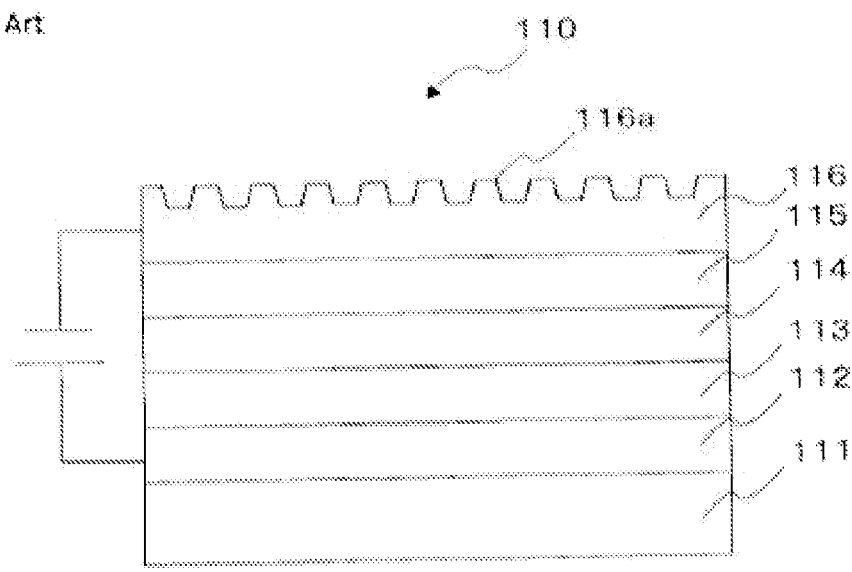
FIG. 2 is an explanatory sectional view showing a configuration according to Patent Literature 2.
Figure 3A:
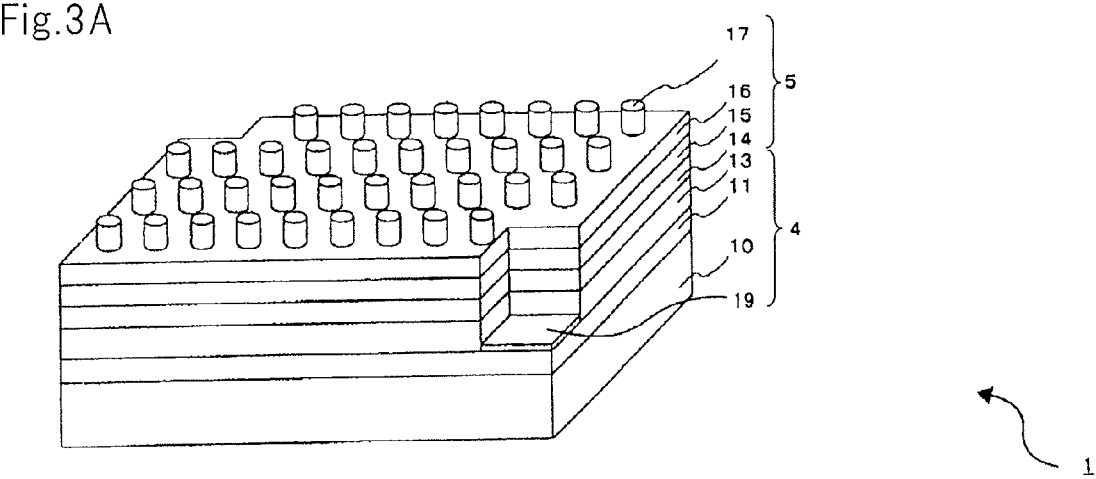
FIG. 3A is a perspective view schematically showing a light emitting element according to a first embodiment.
Figure 3B:
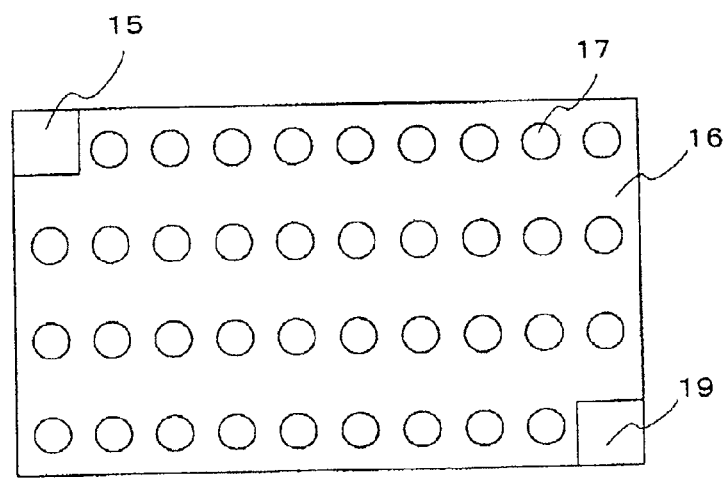
FIG. 3B is a plan view schematically showing the light emitting element according to the first embodiment.

FIG. 3A is a perspective view schematically showing a configuration of a light emitting element according to a first embodiment. FIG. 3B is a plan view schematically showing the configuration of the light emitting element according to the first embodiment. In the light emitting element, individual layers are actually very thin, and there is a large difference in thickness among the layers. It is therefore difficult to draw the layers in accurate scale and proportion. Thus, in the drawings, the layers are not drawn in actual proportion, but are shown schematically.

As shown in FIG. 3A, light emitting element 1 according to the first embodiment includes light source layer 4, and directional control layer 5 that is stacked on light source layer 4 and that serves as an optical element layer, into which light from light source layer 4 enters.

Light source layer 4 includes substrate 10 and a pair of layers, namely, hole-transport layer 11 and electron-transport layer 13, formed on substrate 10. On substrate 10, hole-transport layer 11 and electron-transport layer 13 are stacked in order from substrate 10 side.

Directional control layer 5 is located on a side opposite substrate 10 side of light source layer 4. Directional control layer 5 includes plasmon excitation layer 15 that has a plasma frequency higher than the frequency of light output from light source layer 4, and wave vector conversion layer 17 stacked on plasmon excitation layer 15, which converts light incident from plasmon excitation layer 15 into light having a predetermined exit angle to output the light.

Plasmon excitation layer 15 is sandwiched between two layers having dielectric properties. As two layers having dielectric properties, as shown in FIG. 3A, directional control layer 5 includes high dielectric constant layer 16 sandwiched between plasmon excitation layer 15 and wave vector conversion layer 17, and low dielectric constant layer 14 lower in dielectric constant than high dielectric constant layer 16, which is sandwiched between plasmon excitation layer 15 and electron-transport layer 13.

Concerning the dielectric constants of high dielectric constant layer 16 and low dielectric constant layer 14, when the real part of a complex effective dielectric constant of the incident side portion (substrate 10 side) of plasmon excitation layer 15 is set lower than that of a complex effective dielectric constant of the exit side portion (wave vector conversion layer 17 side) of plasmon excitation layer 15 as described below, light emitting element 1 operates even if the dielectric constant of low dielectric constant layer 14 is higher than that of high electric constant layer 16. Plasma excitation layer 15 is accordingly sandwiched between the pair of layers, namely, high dielectric constant layer 16 and low dielectric constant layer 14.

Optical element 1 according to this embodiment is configured such that an effective dielectric constant of the incident side portion including the entire structure stacked on light source layer 4 side of plasmon excitation layer 15 (hereinafter, simply referred to as incident side portion) is lower than that of the exit side portion including the entire structure stacked on wave vector conversion layer 17 side of plasmon excitation layer 15 and a medium brought into contact with wave vector conversion layer 17 (hereinafter, simply referred to as exit side portion). The entire structure stacked on light source 4 side of plasmon excitation layer 15 includes substrate 10. The entire structure stacked on wave vector conversion layer 17 side of plasmon excitation layer 15 includes wave vector conversion layer 17.

In other words, according to the first embodiment, the effective dielectric constant of the incident side portion including light source layer 4 and low dielectric constant layer 14 with respect to plasmon excitation layer 15 is lower than that of the exit side portion including high dielectric constant layer 16, wave vector conversion layer 17, and the medium with respect to plasmon excitation layer 15.

Specifically, the real part of the complex effective dielectric constant of the incident side portion (substrate 10 side) of plasmon excitation layer 15 is set lower that of the complex effective dielectric constant of the exit side portion (wave vector conversion layer 17 side) of plasmon excitation layer 15.

The complex effective dielectric constant $\varepsilon_{\it{eff}}$ is represented by the following formula (1), in which an x axis and a y axis are directions parallel to the interface of plasmon excitation layer 15, a z axis is a direction vertical to the interface of plasmon excitation layer 15, ω is an angular frequency of light output from light source layer 4, $\varepsilon(\omega, x, y$ and z) is a dielectric constant distribution of dielectrics in the incident side portion and the exit side portion with respect to plasmon excitation layer 15, $k_{spp,z}$ is a z component of a wave number of a surface plasmon, and j is an imaginary unit:

[Formula 1]

$$\varepsilon_{\it{eff}} = \frac{\int\int\int_D \varepsilon(\omega, x, y, z)\exp(2jk_{spp,z}z)}{\int\int\int_D \exp(z)} \quad \text{Formula (1)}$$

Integration range D is a range of three-dimensional coordinates of the incident side portion or the exit side portion with respect to plasmon excitation layer 15. In other words, the range of x-axis and y-axis directions in integration range D is a range up to the outer circumferential surface of the structure included in the incident side portion or the outer circumferential surface of the structure included in the exit surface portion not including the medium, and a range up to the outer edge in a plane parallel to the interface of plasmon excitation layer 15. The range of the z-axis direction in integration range D is the range of the incident side portion or the exit side portion (including medium). When an interface between plasmon excitation layer 15 and a layer having dielectric property and adjacent to plasmon excitation layer 15 is set at a position of z=0, the range of the z-axis direction in integration range D is from this interface to infinity of the adjacent layer side. A direction that is far from this interface is a (+)z direction in the formula (1).

The z component $k_{spp,z}$ of the wave number of the surface plasmon and x and y components $k_{spp}$ of the wave number of the surface plasmon are represented by the following formulas (2) and (3), in which $\varepsilon_{metal}$ is a real part of the dielectric constant of plasmon excitation layer 15, and $k_0$ is the wave number of light in vacuum:

[Formula 2]

$$k_{spp,z} = \sqrt{\varepsilon_{eff} k_0^2 - k_{spp}^2} \quad \text{Formula (2)}$$

[Formula 3]

$$k_{spp} = k_0 \sqrt{\frac{\varepsilon_{eff} \varepsilon_{metal}}{\varepsilon_{eff} + \varepsilon_{metal}}} \quad \text{Formula (3)}$$

Thus, by using the formulas (1) to (3) and substituting $\varepsilon(\omega, x, y \text{ and } z)$ with a dielectric constant distribution $\varepsilon_{in}(\omega, x, y \text{ and } z)$ of the incident side portion of plasmon excitation layer 15 and a dielectric constant distribution $\varepsilon_{out}(\omega, x, y \text{ and } z)$ of the exit side portion of plasmon excitation layer 15, a complex effective dielectric constant $\varepsilon_{effin}$ of the incident side portion and a complex effective dielectric constant $\varepsilon_{effout}$ the exit side portion with respect to plasmon excitation layer 15 are calculated. In reality, a complex effective dielectric constant $\varepsilon_{eff}$ is easily acquired by providing an appropriate initial value as a complex effective dielectric constant $\varepsilon_{eff}$ and repeatedly calculating the formulas (1) to (3). When the dielectric constant of a layer in contact with plasmon excitation layer 15 is very high, the z component $k_{spp,z}$ of the wave number of the surface plasmon in the interface becomes a real number. This is equivalent to not generating any surface plasmon in the interface. The dielectric constant of the layer in contact with plasmon excitation layer 15 accordingly corresponds to the effective dielectric constant in this case.

An effective interaction distance $d_{eff}$ of the surface plasmon is calculated by the following formula (4), in which $e^{-2}$ is intensity of the surface plasmon:

[Formula 4]

$$d_{eff} = \text{Im}\left[\frac{1}{k_{spp,z}}\right] \quad \text{Formula (4)}$$

Low dielectric constant layer 14 of directional control layer 5 has a dielectric constant lower than that of high dielectric constant layer 16. The relationship of $1 \leq \varepsilon_{lr}(\lambda_0) < \varepsilon_{hr}(\lambda_0)$ is satisfied, in which $\varepsilon_l(\lambda_0)$ is a complex dielectric constant of low dielectric constant layer 14, $\varepsilon_{lr}(\lambda_0)$ is its real part, $\varepsilon_{li}(\lambda_0)$ is its imaginary part, $\varepsilon_h(\lambda_0)$ is a complex dielectric constant of high dielectric constant layer 16, $\varepsilon_{hr}(\lambda_0)$ is its real part, $\varepsilon_{hi}(\lambda_0)$ is its imaginary part, and $\lambda_0$ is a wavelength of light incident on the dielectric constant layer in a vacuum.

However, even when the dielectric constant of low dielectric constant layer 14 is higher than that of high dielectric constant layer 16, light emitting element 1 operates as long as the real part of the effective dielectric constant of the portion, which is on the side of low dielectric constant layer 14, of plasmon excitation layer 15 is lower than that of the effective dielectric constant of the portion, which is on the side of high dielectric constant layer 16, of plasmon excitation layer 15. In other words, for dielectric constants of low dielectric constant layer 14 and high dielectric constant layer 16, a range where the real part of the effective dielectric constant of the exit side portion of plasmon excitation layer 15 is maintained higher than that of the effective dielectric constant of the incident side portion is permitted.

As an example indicating the idea of an effective dielectric constant, a case where low dielectric constant layer 14 includes dielectric constant layer A and dielectric constant layer B is discussed, in which high dielectric constant layer 16 includes dielectric constant layer C and dielectric constant layer D, and in which dielectric constant layer B and dielectric constant layer C adjacent to plasmon excitation layer 15 are sufficiently small in film thickness (e.g., 10 nanometers or less). In this case, dielectric constant layer A functions as a low dielectric constant layer, and dielectric constant layer D functions as a high dielectric constant layer. This is because the film thickness of dielectric constant layer B and dielectric constant layer C is very small and has almost no influence on the effective dielectric constant. In other words, complex dielectric constants of low dielectric constant layer 14 and high dielectric constant layer 16 can be set by taking into consideration the complex effective dielectric constant.

An imaginary part $\varepsilon_{li}(\lambda_0)$ and an imaginary part $\varepsilon_{hi}(\lambda_0)$ at an emission frequency are preferably set as small as possible. This facilitates plasmon coupling, enabling reduction of light loss.

Preferably, the imaginary part of a complex dielectric constant is also set as small as possible at the medium adjacent to any layers including light source layer 4 and wave vector conversion layer 17 while excluding hole-transport layer 11, electron-transport layer 13, and plasmon excitation layer 15. Setting the imaginary part of the complex dielectric constant as small as possible facilitates plasmon coupling, enabling reduction of light loss.

As shown in FIGS. 3A and 3B, in light emitting element 1, a part of each layer above hole-transport layer 11 is cut out to expose a part of a surface orthogonal to the thickness direction of hole-transport layer 11, and anode 19 is disposed in a part of exposed hole-transport layer 11. Similarly, in light emitting element 1, parts of high dielectric constant layer 16 and wave vector conversion layer 17 above plasmon excitation layer 15 are cut out to expose a part of a surface orthogonal to the thickness direction of plasmon excitation layer 15, and a part of exposed plasmon excitation layer 15 functions as a cathode. Thus, in the configuration of light emitting element 1 of this embodiment, electrons are injected from plasmon excitation layer 15, and holes (positive holes) are injected from anode 19. Relative positions of electron-transport layer 13 and hole-transport layer 11 of light source layer 14 can be opposite those in this embodiment. A cathode pad made of a material different from that of plasmon excitation layer 15 can be disposed on surface-exposed plasmon excitation layer 15.

The medium around light emitting element 1 can be one of a solid substance, liquid, and gas. Media can be different between the portion of light emitting element 1, which is on the side of substrate 10, and the portion of light emitting element 1, which is on the side of wave vector conversion layer 17.

For hole-transport layer 11, for example, an aromatic amine compound or tetraphenyl di-amine can be used. As hole-transport layer 11, a general LED or a p-type semiconductor layer constituting a semiconductor laser can be used.

For electron-transport layer 13, for example, Alq3, oxadiazole (PDB), or triazole (TAZ) can be used. As electron-transport layer 13, a general LED or an n-type semiconductor layer constituting a semiconductor laser can be used.

FIG. 3A shows a basic configuration of light source layer 4 included in optical element 1 according to the present invention. A configuration where for example, a buffer layer and other layers such as another hole-transport layer and another electron-transport layer are inserted between the layers constituting light source layer 4 can be employed. As the light source layer, a well-known LED structure can be applied.

Light source layer 4 can include a reflection layer (not shown) formed between hole-transport layer 11 and substrate 10 to reflect light from active layer 12. In this configuration, for the reflection layer, for example, a metal film such as Ag or Al, or a dielectric multilayer film can be used.

For low dielectric constant layer 14, for example, a $SiO_2$ nanorod array film, or a thin film or a porous film such as $SiO_2$, $AlF_3$, $MgF_2$, $NalF_6$, NaF, LiF, $CaF_2$, $BaF_2$, or low dielectric constant plastic is preferably used. For low dielectric constant layer 14, a conductive layer doped with an ion, a doner or an acceptor, or a porous film layer mainly made of a conductive material such as ITO, Mg $(OH)_2$: C, $SnO_2$, C12A7, TiO2: Nb, ZnO: $Al_2O_3$, ZnO: $Ga_2O_3$ is particularly preferred. The thickness of low dielectric constant layer 14 is desirably as small as possible.

For high dielectric constant layer 9, for example, a thin film or a porous film made of a high dielectric constant material such as diamond, $TiO_2$, $CeO_2$, $Ta_2O_5$, $ZrO_2$, $Sb_2O_3$, $HfO_2$, $La_2O_3$, $NdO_3$, $Y_2O_3$, ZnO, or $Nb_2O_5$ is preferably used.

In light source layer 4 included in light emitting element 1 of this embodiment, a part of one or both of hole-transport layer 11 and electron-transport layer 13 works as an active layer of the light emitting element on the interface between hole-transport layer 11 and electron-transport layer 13.

Plasmon excitation layer 15 is a particulate layer or a thin-film layer made of a material having a plasma frequency higher than the frequency (emission frequency) of light generated from light source layer 4. In other words, plasmon excitation layer 15 has a negative dielectric constant at an emission frequency generated from light source layer 4.

Materials used for plasmon excitation layer 15 are, for example, gold, silver, copper, platinum, palladium, rhodium, osmium, ruthenium, iridium, iron, tin, zinc, cobalt, nickel, chromium, titanium, tantalum, tungsten, indium, and aluminum, or an alloy of these. Among the materials of plasmon excitation layer 15, gold, silver, copper, platinum, and aluminum, and an alloy mainly containing these are preferable, and gold, silver, and aluminum, and an alloy mainly containing these are particularly preferable.

Plasmon excitation layer 8 is preferably formed with a thickness equal to or less than 200 nanometers, more preferably about 10 nanometers to 100 nanometers. The distance from the interface between high dielectric constant layer 16 and plasmon excitation layer 15 to the interface between electron-transport layer 13 and hole-transport layer 11 is preferably set equal to or less than 500 nanometers. The shorter the distance the better. This distance corresponds to the distance where plasmon coupling occurs between the interface, which is between electron-transport layer 13 and hole-transport layer 11, and plasmon excitation layer 15.

Wave vector conversion layer 17 is an exit layer for taking, by converting a wave vector of light incident on wave vector conversion layer 17, light out of high dielectric constant layer 16 and outputting the light from light emitting element 1. In other words, wave vector conversion layer 17 outputs the light received from high dielectric constant layer 16 from light emitting element 1 by converting its exit angle into a predetermined angle. That is, wave vector conversion layer 17 functions to output the light from light emitting element 1 to be almost orthogonal to the interface with high dielectric constant layer 16.

For wave vector conversion layer 17, for example, a surface-relief grating, a periodic structure represented by a photonic crystal, a quasi-periodic structure (texture structure larger than the wavelength of light from high dielectric constant layer 16) or a quasi-crystal structure, a surface structure having a rough surface, a hologram, and a microlens array are used. The quasi-periodic structure is, for example, an incomplete periodic structure in which a part of a periodic structure is omitted. Among them, the periodic structure represented by the photonic crystal, the quasi-periodic structure, the quasi-crystal structure, and the microlens array are preferably used. This is because not only light taking-out efficiency can be increased but also directionality can be controlled. When the photonic crystal is used, a crystal structure desirably employs a triangular grating structure. Wave vector conversion layer 17 can employ a structure that includes a convex part formed on a flat-plate base. Wave vector conversion layer 17 can be made of a material different from that of high dielectric constant layer 16.

Regarding light emitting element 1 thus configured, an operation of outputting light from wave vector conversion layer 17 will be described.

Electrons are injected from a part of plasmon excitation layer 15 functioning as a cathode, and holes are injected from anode 19. The electrons and the holes injected from a part of plasmon excitation layer 15 and anode 19 into light source layer 14 are respectively passed through electron-transport layer 13 and hole-transport layer 11 to be injected between electron-transport layer 13 and hole-transport layer 11. The electrons and the holes injected between electron-transport layer 13 and hole-transport layer 11 are coupled with electrons and holes in plasmon excitation layer 15 to output light to high dielectric constant layer 16 side.

As described above, light emitting element 1 according to the first embodiment can achieve high luminance as in the case of a LED because the same material as that of a general LED is used to constitute light source layer 4. According to light emitting element 1 of this embodiment, the incident angle of light incident on wave vector conversion layer 17 is determined by plasmon excitation layer 15, by the effective dielectric constant of the incident side portion of plasmon excitation layer 15, by the effective dielectric constant of the exit side portion and by an emission spectrum width which is caused by the electrons and the holes injected between electron-transport layer 13 and hole-transport layer 11, and hence directivity of the output light from light emitting element 1 is not limited to that of light source layer 4. In light emitting element 1 of this embodiment, through the application of plasmon coupling in the radiation process, directivity of the output light can be increased by narrowing the radiation angle of the output light from light emitting element 1.

As a result, according to this embodiment, luminance and directivity of the output light can be simultaneously increased. According to this embodiment, since the directivity of the output light from light emitting element 1 is increased, the etendue of the output light can be reduced.

The manufacturing process of light emitting element 1 according to the first embodiment is similar to that of a second embodiment described below except for no inclusion of an active layer forming step. Thus, description of the manufacturing process of light emitting element 1 according to the first embodiment is omitted.

Hereinafter, light emitting elements of other embodiments are described. The light emitting elements of the other embodiments are different only as regards the configuration of light source layer 4 or directional control layer 5 from light emitting element 1 of the first embodiment. Thus, only a light source layer or a directional control layer different from that of the first embodiment is described. Layers of the light emitting elements of the other embodiments similar to those of light source layer 4 and directional control layer 5 of the first embodiment are denoted by similar reference numerals, and description thereof is omitted.

Second Embodiment

Figure 4A:
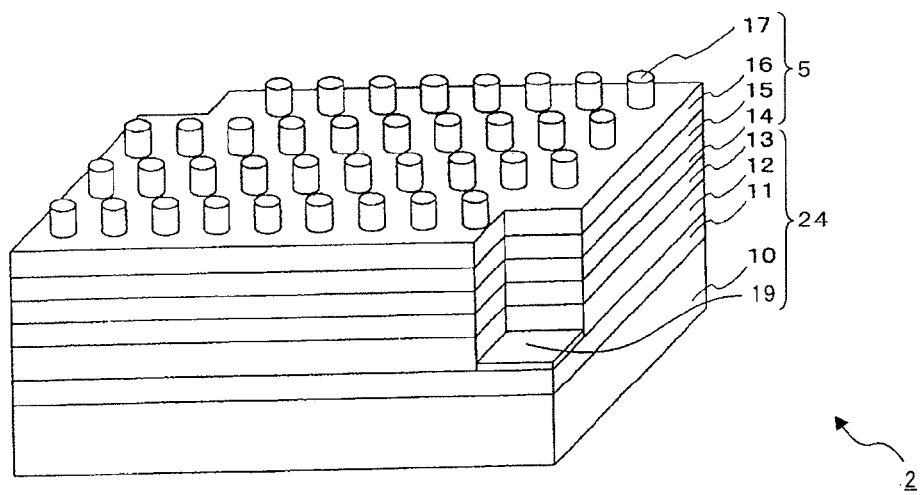
FIG. 4A is a perspective view schematically showing a light emitting element according to a second embodiment.
Figure 4B:
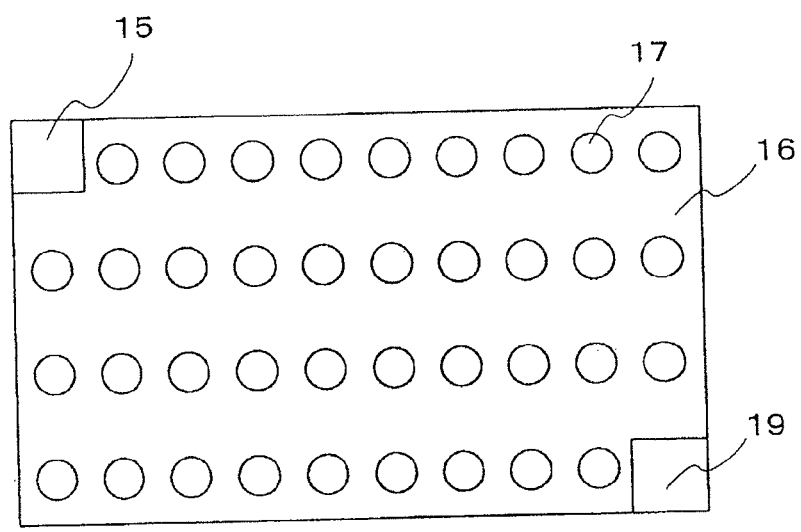
FIG. 4B is a plan view schematically showing the light emitting element according to the second embodiment.

FIG. 4A is a perspective view schematically showing a light emitting element according to a second embodiment. FIG. 4B is a plan view schematically showing the light emitting element according to the second embodiment.

As shown in FIGS. 4A and 4B, light emitting element 2 according to the second embodiment includes light source layer 24, and directional control layer 5 that is stacked on light source layer 24 and that serves as an optical element layer, into which light from light source layer 24 enters. Directional control layer 5 included in light emitting element 2 of the second embodiment is similar to that of the first embodiment, and thus description thereof is omitted. Light source layer 24 included in light emitting element 2 of the second embodiment is different from light source layer 4 of the first embodiment in that active layer 12 is formed between hole-transport layer 11 and electron-transport layer 13.

For active layer 12 of light source layer 24, for example, an inorganic material (semiconductor) such as InGaN, AlGaAs, AlGaInP, GaN, ZnO, or diamond, or an organic material (semiconductor material) such as (thiophene/phenylene) cooligomer or Alq3 is used. Active layer 12 preferably employs a quantum well structure.

In light emitting element 2 of the second embodiment, the distance from the interface between high dielectric constant layer 16 and plasmon excitation layer 15 to the interface between electron-transport layer 13 and active layer 12 is preferably set equal to or less than 500 nanometers. The shorter the distance the better. This distance corresponds to the distance where plasmon coupling occurs between active layer 12 and plasmon excitation layer 15.

In light emitting element 2 of the second embodiment, electrons and holes injected from a part of plasmon excitation layer 15 and anode 19 into light source layer 24 are respectively passed through electron-transport layer 13 and hole-transport layer 11 to be injected into active layer 12. The electrons and the holes injected into active layer 12 are coupled with electrons and holes in plasmon excitation layer 15 to output light to high dielectric constant layer 16 side. The light thus entered into high dielectric constant layer 16 is output from wave vector conversion layer 17.

Figure 5A:
FIG. 5A is an explanatory sectional view showing a manufacturing process of the light emitting element according to the second embodiment.
Figure 5B:
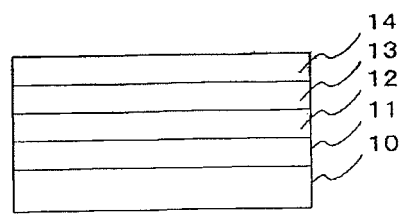
FIG. 5B is an explanatory sectional view showing the manufacturing process of the light emitting element according to the second embodiment.
Figure 5C:
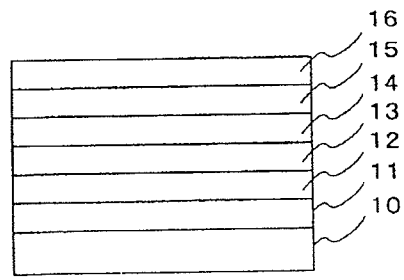
FIG. 5C is an explanatory sectional view showing the manufacturing process of the light emitting element according to the second embodiment.

FIGS. 5A to 5C show the manufacturing process of light emitting element 2 according to the second embodiment, which is only an example and does not limit the manufacturing process. A general well-known step can be employed for stacking hole-transport layer 11, active layer 12, and electron-transport layer 13 on substrate 10 as shown in FIG. 5A, and thus description thereof is omitted. As described above, in the manufacturing process of light emitting element 1 according to the first embodiment, only the step of forming active layer 12 is omitted.

Subsequently, for example, by using physical vapor deposition, electron beam deposition, or sputtering, low dielectric constant layer 14, plasmon excitation layer 15, and high dielectric constant layer 16 are stacked in order on electron-transport layer 13 as shown in FIGS. 5B and 5C.

Figure 6A:
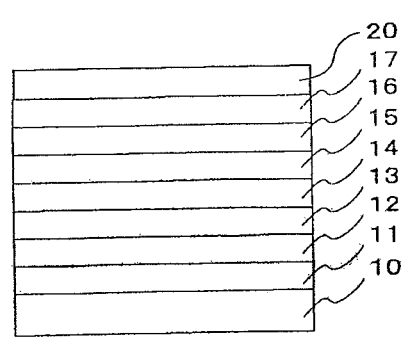
FIG. 6A is an explanatory sectional view showing a forming process of a wave vector conversion layer including a photonic crystal in the light emitting element according to the second embodiment.
Figure 6B:
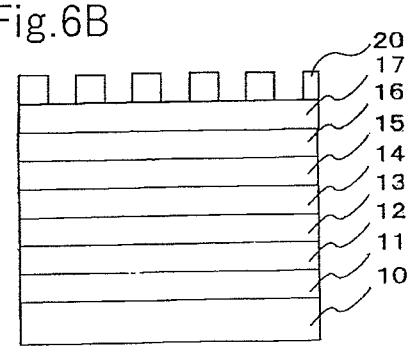
FIG. 6B is an explanatory sectional view showing the forming process of the wave vector conversion layer including the photonic crystal in the light emitting element according to the second embodiment.
Figure 6C:
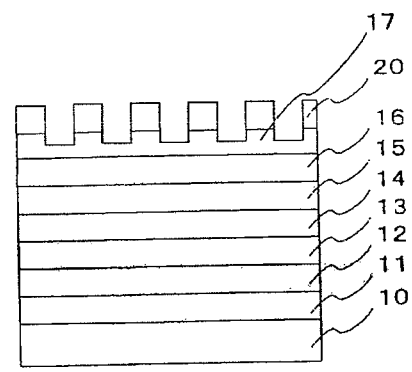
FIG. 6C is an explanatory sectional view showing the forming process of the wave vector conversion layer including the photonic crystal in the light emitting element according to the second embodiment.
Figure 6D:
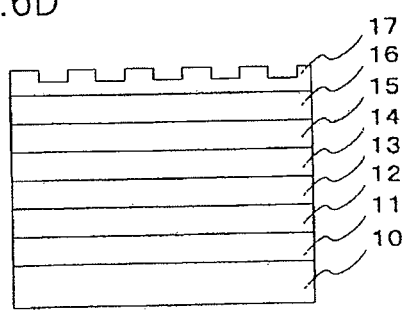
FIG. 6D is an explanatory sectional view showing the forming process of the wave vector conversion layer including the photonic crystal in the light emitting element according to the second embodiment.

FIGS. 6A to 6D show the process of forming wave vector conversion layer 17 by a photonic crystal. As shown in FIG. 6A, wave vector conversion layer 17 is formed on high dielectric constant layer 16, and resist film 20 is deposited on wave vector conversion layer 17 by spin coating. As shown in FIG. 6B, a negative pattern of the photonic crystal is transferred to resist film 20 by nano imprinting, photolithography, or electron beam lithography. Then, as shown in FIG. 6C, wave vector conversion layer 17 is etched to a desired width by dry etching. As shown in FIG. 6D, resist film 20 is then peeled off. Lastly, parts of the surfaces of plasmon excitation layer 15 and hole-transport layer 11 are etched to be exposed, and anode 19 is disposed in a part of hole-transport layer 11, thereby completing light emitting element 2.

Third Embodiment

Figure 7A:
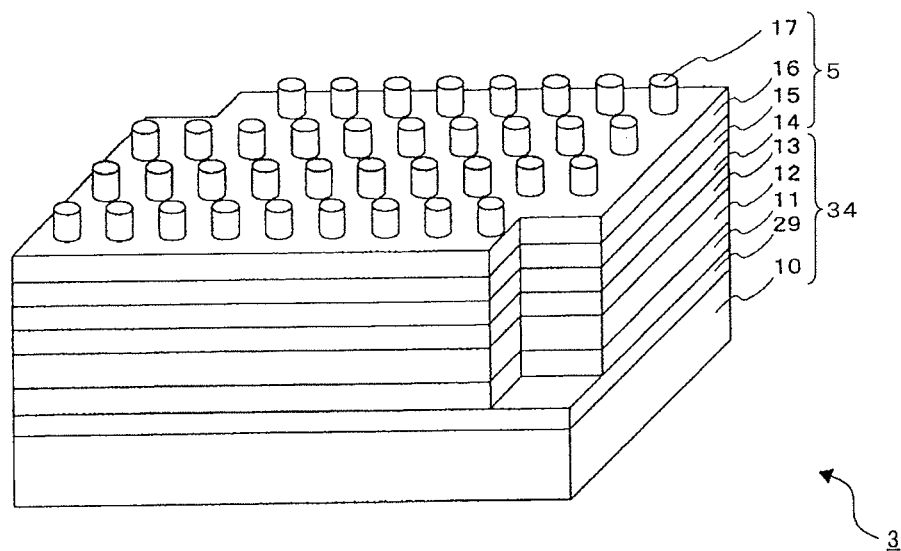
FIG. 7A is a perspective view schematically showing a light emitting element according to a third embodiment.
Figure 7B:
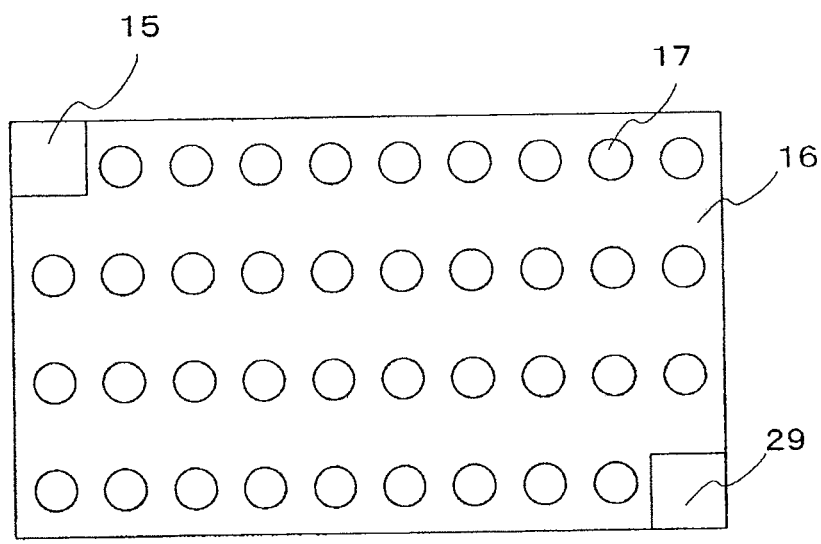
FIG. 7B is a plan view schematically showing the light emitting element according to the third embodiment.

FIG. 7A is a perspective view schematically showing a light emitting element according to a third embodiment. FIG. 7B is a plan view schematically showing the light emitting element according to the third embodiment.

As shown in FIGS. 7A and 7B, light emitting element 3 according to the third embodiment includes light source layer 34, and directional control layer 5 that is stacked on light source layer 34 and that serves as an optical element layer, into which light from light source layer 34 enters. Directional control layer 5 included in light emitting element 3 of the third embodiment is similar to that of the first embodiment, and thus description thereof is omitted. Light source layer 34 included in light emitting element 3 of the third embodiment is different from light source layer 24 of the second embodiment in that anode layer 29 that serves as an anode is formed on the entire surface of substrate 10 between substrate 10 and hole-transport layer 11.

In the third embodiment, anode layer 29 functions as a reflection layer to reflect light from active layer 12. According to the third embodiment, therefore, the light radiated from active layer 12 to substrate 10 side can be reflected to wave vector conversion layer 17, improving efficiency in picking up light from active layer 12. For anode layer 29, for example, a thin metal film of Ag, Al or an alloy mainly containing these can be used.

In the third embodiment, anode layer 20 also functions as a heat radiation plate. Thus, light source layer 34 can prevent reduction of internal quantum efficiency caused by heat generated during light emission.

Anode layer 29 increases hole mobility. In most cases, the hole mobility is lower than electron mobility. This causes hole injection to lag behind electron injection, limiting internal quantum efficiency. In other words, the inclusion of anode layer 29 enables light source layer 34 to improve internal quantum efficiency. Further, since the inclusion of anode layer 29 improves the hole mobility in an in-plane direction of light emitting element 3, light source layer 34 can emit light within the plane more uniformly.

In plasmon excitation layer 15, a surface of which is partly exposed, a cathode pad made of a material different from that of plasmon excitation layer 15 can be disposed on this exposed part, and an anode pad made of a material different from that of anode layer 29 can be disposed on anode layer 29.

Fourth Embodiment

Figure 8A:
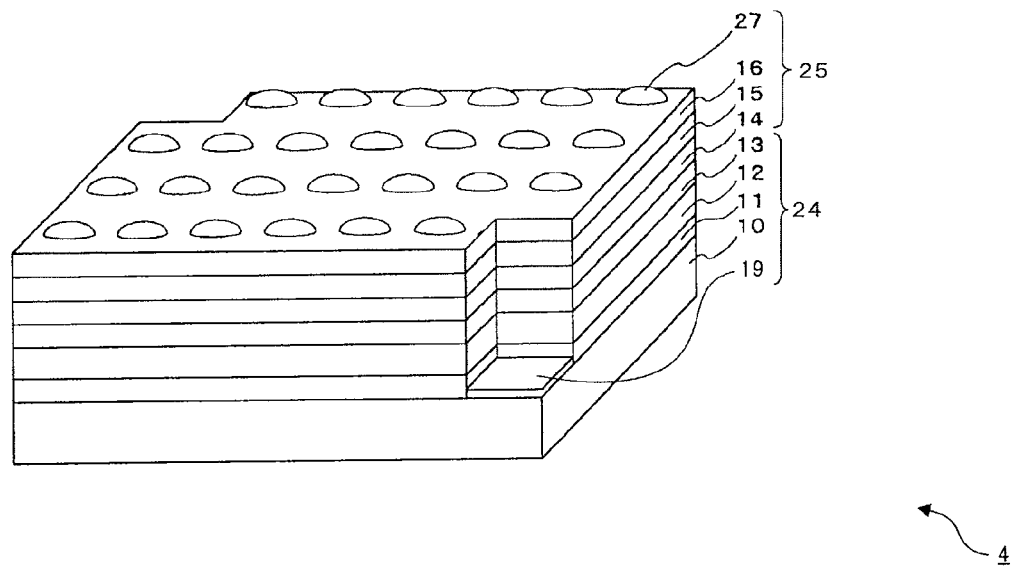
FIG. 8A is a perspective view schematically showing a light emitting element according to a fourth embodiment.

FIG. 8A is a perspective view schematically showing a light emitting element according to a fourth embodiment.

Figure 8B:
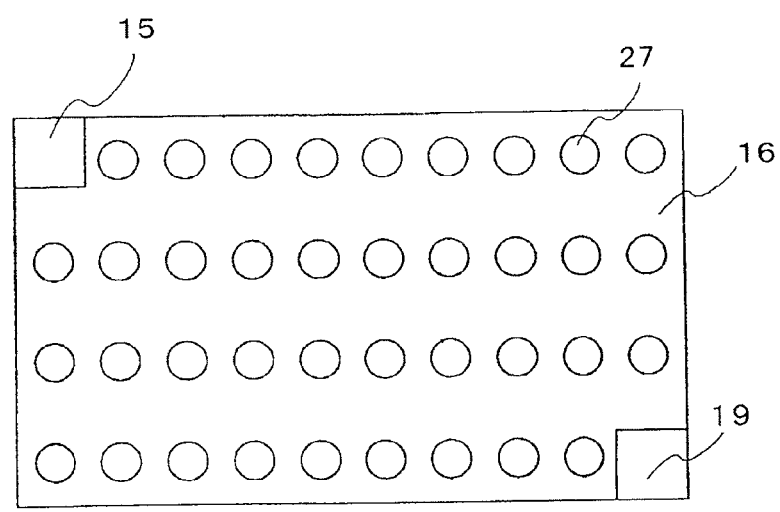
FIG. 8B is a plan view schematically showing the light emitting element according to the fourth embodiment.

FIG. 8B is a plan view schematically showing the light emitting element according to the fourth embodiment. As shown in FIGS. 8A and 8B, directional control layer 25 included in light emitting element 6 of the fourth embodiment includes wave vector conversion layer 27 that includes a microlens array. Directional control layer 25 of this embodiment provides effects similar to those of directional control layer 5 having wave vector conversion layer 17 made of the photonic crystal in the abovementioned embodiment.

Light source layer 24 of this embodiment includes anode 19 disposed in a part of hole-transport layer 11. However, as in the case of the second embodiment, anode layer 29 can be formed between substrate 10 and hole-transport layer 11.

Figure 9A:
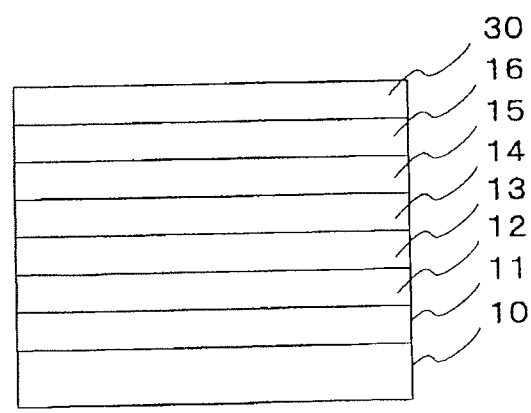
FIG. 9A is an explanatory sectional view showing a forming process of a wave vector conversion layer including a microlens array in a light emitting element according to a fifth embodiment.
Figure 9B:
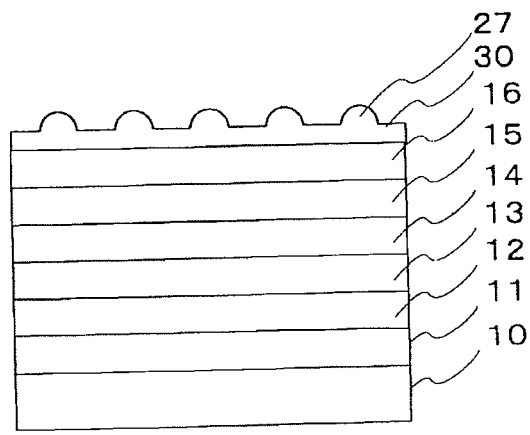
FIG. 9B is an explanatory sectional view showing the forming process of the wave vector conversion layer including the microlens array in the light emitting element according to the fifth embodiment.

FIGS. 9A and 9B are explanatory sectional views showing the manufacturing process of a configuration where wave vector conversion layer 27 that includes the microlens array is stacked on high dielectric constant layer 16. In the configuration including wave vector conversion layer 27 that has the microlens array, as in the case of the forming process shown in FIGS. 6A to 6D, the layers that include hole-transport layer 11 to high dielectric constant layer 16 are stacked on substrate 10. Thus, description thereof is omitted.

As shown in FIGS. 9A and 9B, after the layers including hole-transport layer 11 to high dielectric constant layer 16 have been stacked on substrate 10 by using the forming process shown in FIGS. 6A to 6D, wave vector conversion layer 27 that includes the microlens array is formed on the surface of high dielectric constant layer 16. This is only an example, and does not limit the manufacturing method. After deposition of UV cured resin 30 on the surface of high dielectric constant layer 16 by spin coating, a desired lens array pattern is formed in UV cured resin 30 by using nano imprinting. UV cured resin 30 is then irradiated with light to be cured, thereby forming wave vector conversion layer 27 including the microlens array.

Fifth Embodiment

Figure 10:
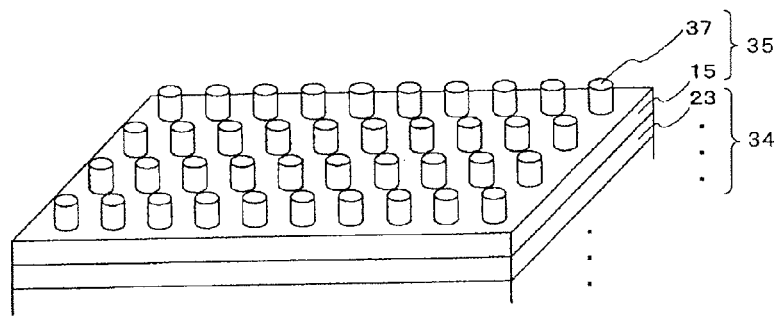
FIG. 10 is a perspective view schematically showing a directional control layer included in the light emitting element according to the fifth embodiment.

FIG. 10 is a perspective view showing a directional control layer included in a light emitting element according to a fifth embodiment. As shown in FIG. 10, directional control layer 35 included in the light emitting element according to the fifth embodiment includes plasmon excitation layer 15 staked on electron-transport layer 23 of light source layer 34, and wave vector conversion layer 37 stacked on plasmon excitation layer 15.

Directional control layer 35 of the fifth embodiment corresponds to a high dielectric constant layer because wave vector conversion layer 37 also functions as a high dielectric constant layer. Electron-transport layer 23 of light source layer 34 corresponds to a low dielectric constant layer because it also functions as a low dielectric constant layer of directional control layer 35. The dielectric constant of electron-transport layer 23 of light source layer 34 of the fifth embodiment is accordingly set lower than that of wave vector conversion layer 37.

However, even when the dielectric constant of wave vector conversion layer 37 is lower than that of electron-transport layer 23, directional control layer 35 operates as long as the real part of the effective dielectric constant of the portion, which is on the side of wave vector conversion layer 37, of plasmon excitation layer 15 is higher than that of the effective dielectric constant of electron-transport layer 23 side of plasmon excitation layer 15. In other words, for the dielectric constants of wave vector conversion layer 37 and electron-transport layer 23, a range where the real part of the effective dielectric constant of the exit side portion of plasmon excitation layer 15 is maintained higher than that of the effective dielectric constant of the incident side portion is permitted.

According to the fifth embodiment thus configured, effects similar to those of the first to fourth embodiments can be provided, and the manufacturing process can be simpler than those of the first to fourth embodiments.

Sixth Embodiment

Figure 11:
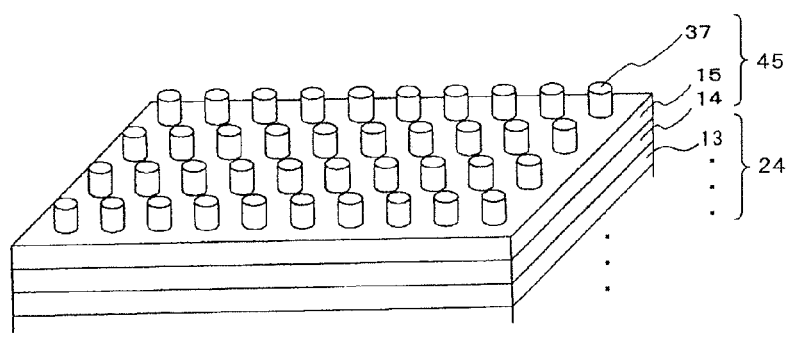
FIG. 11 is a perspective view schematically showing a directional control layer included in a light emitting element according to a sixth embodiment.

FIG. 11 is a perspective view showing a directional control layer included in a light emitting element according to a sixth embodiment. As shown in FIG. 11, directional control layer 45 of the sixth embodiment includes low dielectric constant layer 14 stacked on electron-transport layer 13 of light source layer 24, plasmon excitation layer 15 staked on low dielectric constant layer 14, and wave vector conversion layer 37 stacked on plasmon excitation layer 15.

Directional control layer 45 of the sixth embodiment corresponds to a high dielectric constant layer because wave vector conversion layer 37 also functions as a high dielectric constant layer.

According to the sixth embodiment thus configured, effects similar to those of the first to fourth embodiments can be provided, and a manufacturing process can be simpler than those of the first to fourth embodiments.

Seventh Embodiment

Figure 12:
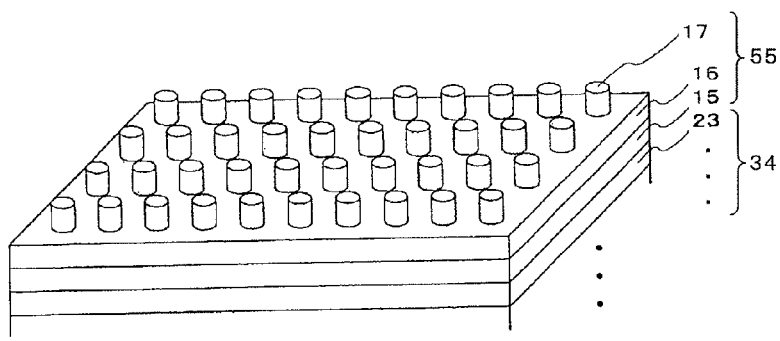
FIG. 12 is a perspective view schematically showing a directional control layer included in a light emitting element according to a seventh embodiment.

FIG. 12 is a perspective view showing a directional control layer included in a light emitting element according to a seventh embodiment. As shown in FIG. 12, directional control layer 55 of the seventh embodiment includes plasmon excitation layer 15 stacked on electron-transport layer 23 of light source layer 34, high dielectric constant layer 16 staked on plasmon excitation layer 15, and wave vector conversion layer 37 stacked on high dielectric constant layer 16.

Directional control layer 55 of the seventh embodiment corresponds to a low dielectric constant layer because electron-transport layer 23 of light source layer 34 also functions as a low dielectric constant layer of directional control layer 55.

According to the seventh embodiment thus configured, effects similar to those of the first to fourth embodiments can be provided, and a manufacturing process can be simpler than those of the first to fourth embodiments.

Eighth Embodiment

Figure 13:
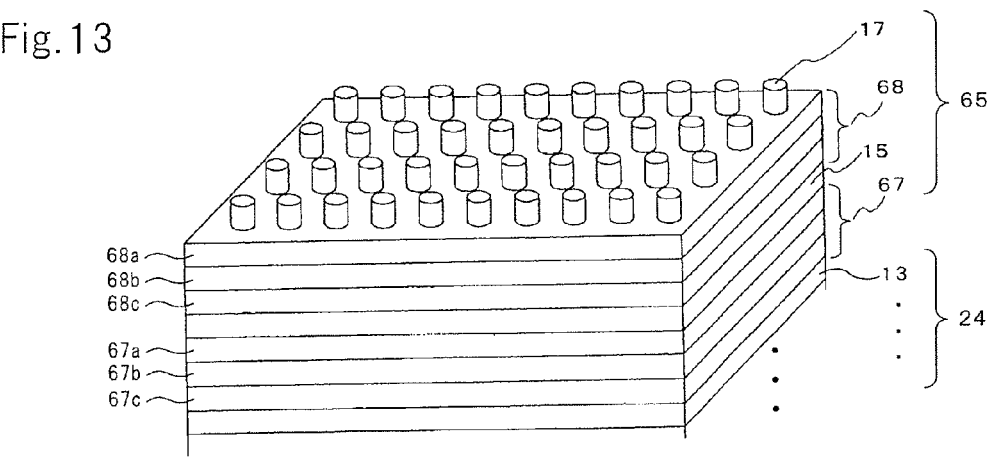
FIG. 13 is a perspective view schematically showing a directional control layer included in a light emitting element according to an eighth embodiment.

FIG. 13 is a perspective view showing a directional control layer included in a light emitting element according to an eighth embodiment. As shown in FIG. 13, directional control layer 65 of the eighth embodiment is similar in configuration to directional control layer 5 of the first embodiment, but different in that low dielectric constant layer 14 and high dielectric constant layer 16 of the first embodiment each includes a plurality of stacked dielectric layers.

Specifically, directional constant layer 65 of the eighth embodiment includes low dielectric constant layer group 67 formed by stacking a plurality of dielectric layers 67a to 67c, and high dielectric constant layer group 68 formed by stacking a plurality of dielectric layers 68a to 68c.

In low dielectric constant layer group 67, the plurality of dielectric layers 67a to 67c are arranged so that dielectric constants can be monotonously lower from near electron-transport layer 13 of light source layer 24 to plasmon excitation layer 15. Similarly, in high dielectric constant layer group 68, the plurality of dielectric layers 68a to 68c are arranged so that dielectric constants can be monotonously lower from near plasmon excitation layer 15 to wave vector conversion layer 17 side made of a photonic crystal.

The overall thickness of low dielectric constant layer group 67 is set equal to that of a low dielectric constant layer in an embodiment where a directional control layer independently includes the low dielectric constant layer. Similarly, the overall thickness of high dielectric constant layer group 68 is set equal to that of a high dielectric constant layer in an embodiment where a directional control layer independently includes the high dielectric constant layer. Each of low dielectric constant layer group 67 and high dielectric constant layer group 68 is shown in a three-layer structure. However, these groups can be formed in a structure of, for example, two to five layers. When necessary, the numbers of dielectric layers constituting the low dielectric constant layer group and the high dielectric constant layer group can be different from each other, or only the low dielectric constant layer group or the high dielectric constant layer group can include a plurality of dielectric layers.

The inclusion of the pluralities of dielectric layers 67a to 67c and 68a to 68c in low dielectric constant layer group 67 and high dielectric constant layer group 68 enables appropriate setting of dielectric constants of dielectric layers 67a and 68c adjacent to the interface of plasmon excitation layer 15 and suitable matching of refractive indexes among electron-transport layer 13 of light source layer 24, wave vector conversion layer 17 or a medium such as outside air, and dielectric layers 67c and 68a adjacent to these layers. In other words, high dielectric constant layer group 68 can reduce the refractive index difference on the interface with wave vector conversion layer 17 or the medium such as outside air, and low dielectric constant layer group 67 can reduce the refractive index difference on the interface with electron-transport layer 13 of light source layer 24.

According to directional control layer 65 of the eighth embodiment thus configured, the dielectric constants of dielectric layers 67a and 68c adjacent to plasmon excitation layer 15 can be appropriately set, and the refractive index differences on the interfaces with electron-transport layer 13 of light source layer 24 and wave vector conversion layer 17 can be set small. As a result, directional control layer 65 can reduce light loss more and increase use efficiency of the light from light source layer 4 more.

In place of low dielectric constant layer group 67 and high dielectric constant layer group 68, a single-layer film having a dielectric constant monotonously changed therein can be used. In the case of this configuration, a high dielectric constant layer has a dielectric constant distribution gradually reduced from the portion, which is on the side of plasmon excitation layer 15, to the portion, which is on the side of wave vector conversion layer 17. Similarly, a low dielectric constant layer has a dielectric constant distribution gradually reduced from the portion, which is on the side of electron-transport layer 13, of light source layer 24 to the portion, which is on the side of plasmon excitation layer 15.

Ninth Embodiment

Figure 14:
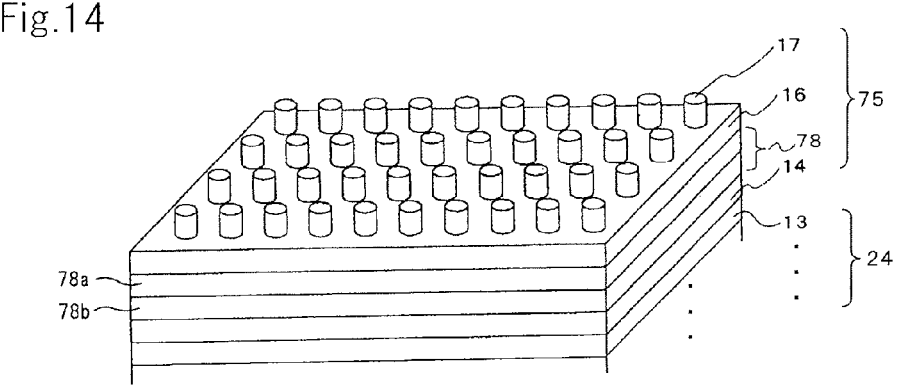
FIG. 14 is a perspective view schematically showing a directional control layer included in a light emitting element according to a ninth embodiment.

FIG. 14 is a perspective view showing a directional control layer included in a light emitting element according to a ninth embodiment. As shown in FIG. 14, directional control layer 75 of the ninth embodiment is similar in configuration to directional control layer 5 of the first embodiment, but different in that plasmon excitation layer group 78 includes a plurality of metal layers 78a and 78b.

In plasmon excitation layer group 78 of directional control layer 75 according to the ninth embodiment, metal layers 78a and 78b are made of different metallic materials to be stacked. This enables plasmon excitation layer group 78 to adjust the plasma frequency.

To adjust the plasma frequency to be high in plasmon excitation layer group 78, for example, metal layers 78a and 78b are respectively made of Ag and Al. To adjust the plasma frequency to be low in plasmon excitation layer group 78, for example, different metal layers 78a and 78b are respectively made of Ag and Au. Plasmon excitation layer group 78 is shown to have a two-layered structure as an example. Needless to say, however, plasmon excitation layer group 78 can include three or more metal layers when necessary.

According to directional control layer 75 of the ninth embodiment thus configured, plasmon excitation layer group 78 includes the plurality of metal layers 78a and 78b. This enables adjustment of an effective plasma frequency in plasmon excitation layer group 78 close to the emission frequency of active layer 12. As a result, electrons or holes in plasmon excitation layer group 78 are appropriately coupled with electrons or holes in active layer 12 to increase output efficiency.

Tenth Embodiment

Figure 15A:
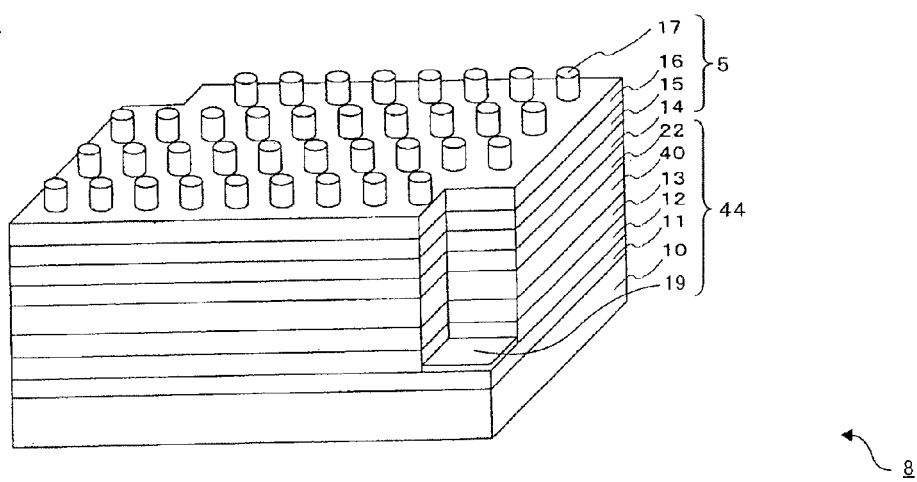
FIG. 15A is a perspective view schematically showing a light emitting element according to a tenth embodiment.
Figure 15B:
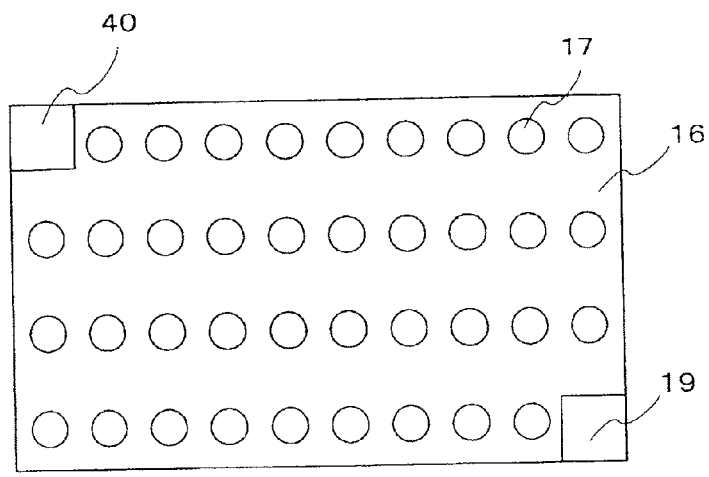
FIG. 15B is a plan view schematically showing the light emitting element according to the tenth embodiment.

FIG. 15A is a perspective view schematically showing a light emitting element according to a tenth embodiment. FIG. 15B is a plan view schematically showing the light emitting element according to the tenth embodiment.

As shown in FIGS. 15A and 15B, light source layer 44 included in light emitting element 8 of the tenth embodiment has a general LED structure where transparent electrode layer 40 is staked on electron-transport layer 13 of light source layer 24 of the second embodiment. In other words, light source layer 44 includes transparent electrode layer 40 stacked on a side opposite substrate 10 side. Light source layer 44 includes another active layer 22 that is different from active layer 12 on this LED structure.

Light source layer 4 of the first embodiment can include an active layer where electrons and holes are generated by light from the interface of hole-transport layer 11 and electron-transport layer 13 as in the case of abovementioned another layer 22, and a transparent electrode layer. In light source layer 44 of this embodiment, anode 19 is disposed in a part of hole-transport layer 11. However, as in the case of the third embodiment, anode layer 29 can be formed between substrate 10 and hole-transport layer 11.

In light emitting element 8 of the tenth embodiment, through injection of current to light source layer 44, the light from active layer 12 excites electrons and holes in another active layer 22. The electrons and the holes generated in another active layer 22 are plasmon-coupled with the electrons and the holes in plasmon excitation layer 15 as described above to output light of a predetermined wavelength in a predetermined direction determined by characteristics of directional control layer 5.

According to light emitting element 8 of the tenth embodiment thus configured, when light having a desired wavelength is output, a selection width of light emitting materials used for active layers can be widened. For example, as a light emitting material to acquire green output light, there is known an inorganic material having high light emitting efficiency through light injection while no inorganic material having high light emitting efficiency through current injection is known. According to this embodiment, when a light emitting material having such characteristics is used, the inclusion of light source layer 34 having active layer 12 and another active layer 22 enables injection of light acquired by first injecting current to active layer 12 to another active layer 22. Thus, light emitting efficiency of light source layer 44 can be increased by efficiently utilizing characteristics of the light emitting material used for another active layer 22.

(Light Source Device of Embodiment)

Figure 16:
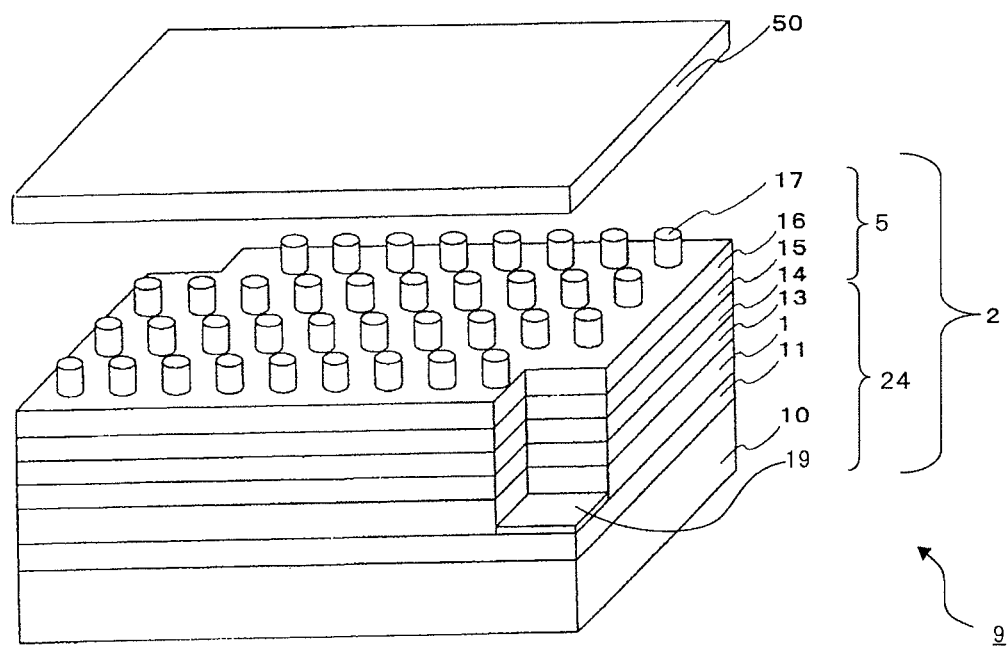
FIG. 16 is a perspective view showing a ½ wavelength plate for axially symmetric polarization applied to the light emitting element according to an embodiment.

Next, a light source device that includes an axially symmetric polarization ½ wavelength plate disposed on the exit side of light emitting element 2 of the abovementioned second embodiment is described. FIG. 16 is an explanatory perspective view showing the axially symmetric polarization ½ wavelength plate applied to abovementioned light emitting element 2.

As shown in FIG. 16, light source device 9 of the embodiment includes, as a polarizing conversion element for arranging axially symmetric polarized light incident from light emitting element 2 in a predetermined polarized state, axially symmetric polarization ½ wavelength plate 50 for linearly polarizing the light incident from light emitting element 2. Axially symmetric polarization ½ wavelength plate 50 is located on wave vector conversion layer 17 side of light emitting element 2. Linearly polarizing the light output from light emitting element 2 by axially symmetric polarization ½ wavelength plate 50 can achieve output light having a uniform in polarization state. Arranging the axially symmetric polarized light in the predetermined polarized state by the polarizing conversion element is not limited to linear polarization. Circular polarization is also included. Needless to say, the light source device that includes axially symmetric polarization ½ wavelength plate 50 can be applied to any of the light emitting elements of the abovementioned first to tenth embodiments.

Figure 17:
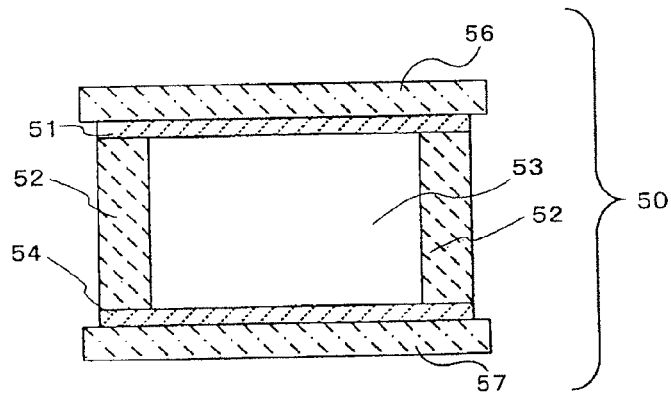
FIG. 17 is a longitudinal sectional view showing the structure of the ½ wavelength plate for axially symmetric polarization applied to the light emitting element according to the embodiment.

FIG. 17 is a vertical sectional view showing the structure of axially symmetric polarization ½ wavelength plate 50. The configuration of axially symmetric polarization ½ wavelength plate 50 is only an example, and thus is in no way limitative. As shown in FIG. 17, axially symmetric polarization ½ wavelength plate 50 includes a pair of glass substrates 56 and 57 in which oriented films 51 and 54 are respectively formed, liquid crystal layer 53 located by sandwiching oriented films 51 and 54 of glass substrates 56 and 57 opposite to each other between glass substrates 56 and 57, and spacer 52 located between glass substrates 56 and 57.

For liquid crystal layer 53, a refractive index ne is larger than a refractive index no, where no is the refractive index for ordinary light, and ne is the refractive index for extraordinary light. A thickness d of liquid crystal layer 53 satisfies $(ne-no) \times d = \lambda/2$, where $\lambda$ is a wavelength of incident light in vacuum.

Figure 18A:
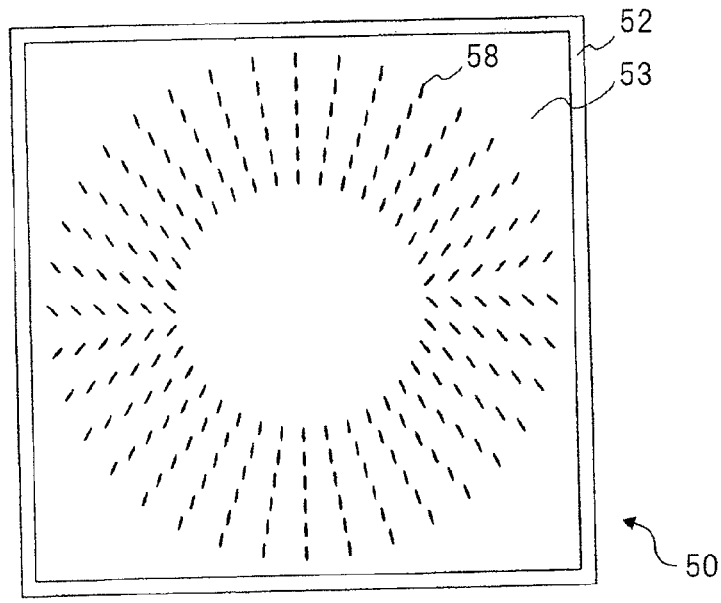
FIG. 18A is an explanatory view schematically showing the ½ wavelength plate for axially symmetric polarization applied to the light emitting element according to the embodiment.
Figure 18B:
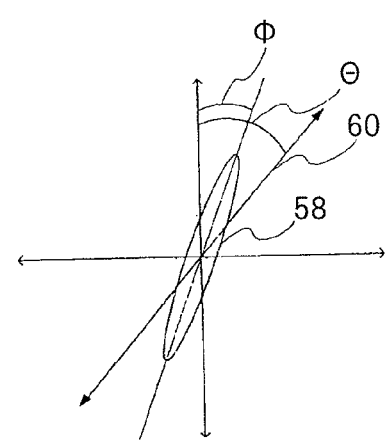
FIG. 18B is an explanatory view schematically showing the ½ wavelength plate for axially symmetric polarization applied to the light emitting element according to the embodiment.

FIGS. 18A and 18B are explanatory schematic views showing axially symmetric polarization ½ wavelength plate 50. FIG. 18A is a transverse sectional view showing a state where liquid crystal layer 53 of axially symmetric polarization ½ wavelength plate 50 is cut in parallel to the principal surfaces of glass substrates 56 and 57. FIG. 18B is an explanatory schematic view showing the orientation direction of liquid crystal molecules 58.

As shown in FIG. 18A, liquid crystal molecules 58 are concentrically arranged around axially symmetric polarization ½ wavelength plate 50. As shown in FIG. 18B, liquid crystal molecules 58 are oriented in a direction that satisfies the relationship of $\theta = 2\phi$ or $\theta = \phi + 90$, where $\phi$ is an angle formed between the main axis of liquid crystal molecules 58 and the coordinate axis near the main axis and $\theta$ is an angle formed between the coordinate axis and the polarizing direction.

Figure 19:
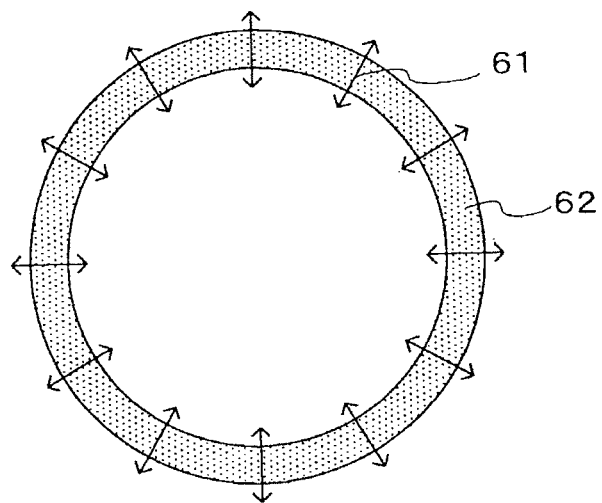
FIG. 19 schematically shows a far-field pattern and a polarizing direction of output light when no ½ wavelength plate for axially symmetric polarization is included in the light emitting element according to the embodiment.

FIG. 19 shows far-field pattern 62 of output light when the light emitting element does not include an axially symmetric polarization ½ wavelength plate. In the abovementioned first to tenth embodiments, polarized light output from plasmon excitation layer 15 via plasmon coupling is only TM polarized light. Thus, as shown in FIG. 19, far-field pattern 62 of the output light from light emitting element 2 becomes axially polarized light whose polarizing direction is radial.

Figure 20:
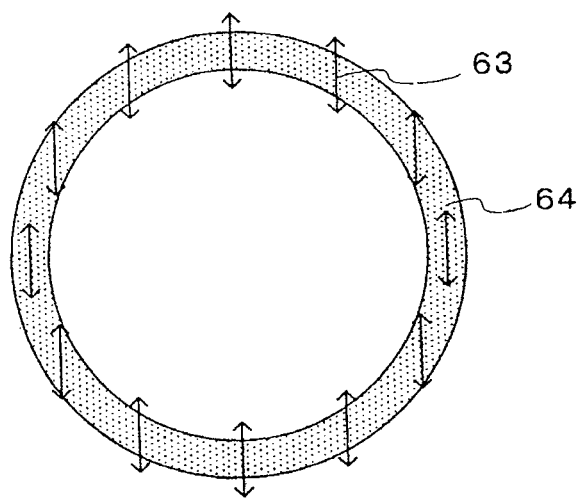
FIG. 20 schematically shows a far-field pattern and a polarizing direction of output light when a ½ wavelength plate for axially symmetric polarization is included in the light emitting element according to the embodiment.

FIG. 20 shows far-field pattern 64 of output light that passed through axially symmetric polarization ½ wavelength plate 50. According to light emitting element 2, as shown in FIG. 20, the operation of axially symmetric polarization ½ wavelength plate 50 enables acquisition of output light where polarizing direction 63 in the plane is uniform.

The light emitting element of this embodiment, which is suitably used for the light source of an image display device, can be used for a light source included in a projection display device, the near-field light source of a liquid crystal display panel (LCD), a portable telephone as a backlight, or an electronic device such as a PDA (Personal Data Assistant).

Example 1

Figure 21:
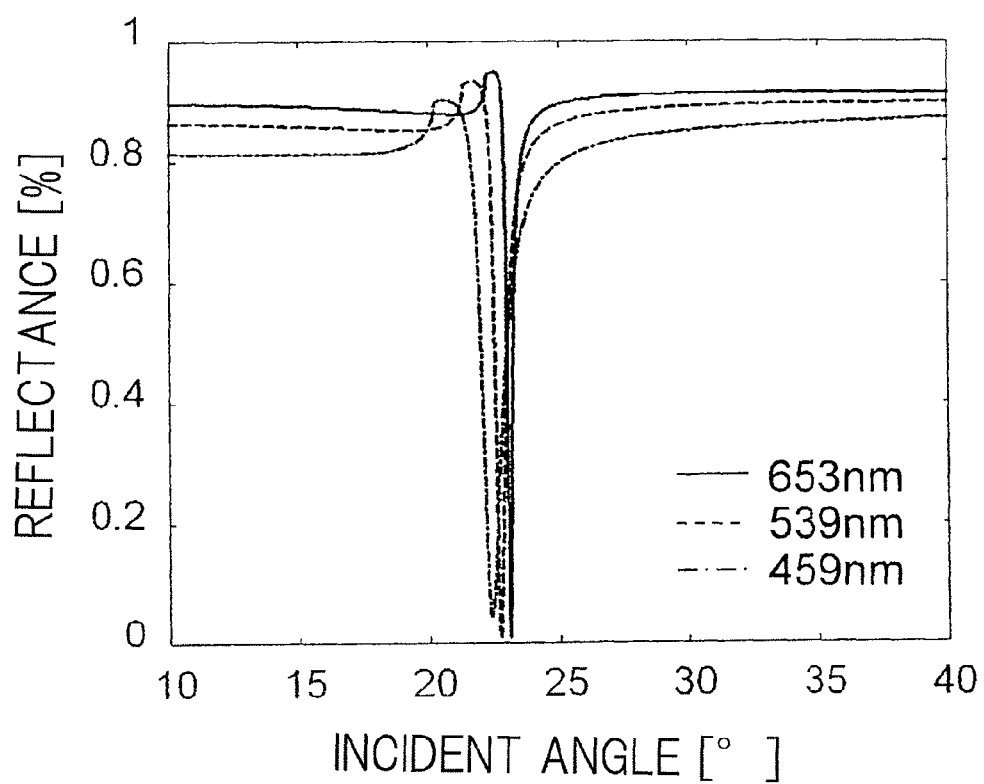
FIG. 21 is an explanatory view showing plasmon resonance characteristics according to the embodiment.

FIG. 21 illustrates plasmon resonance characteristics according to the abovementioned embodiment. FIG. 21 shows the relationship between the incident angle and reflectance, when in the light emitting element using $TiO_2$ for high dielectric constant layer 16, Ag for plasmon excitation layer 15, and porous $SiO_2$ for low dielectric constant layer 14, lights having wavelengths of 653 nanometers, 539 nanometers, and 459 nanometers enter into plasmon excitation layer 15. High dielectric constant layer 16 and low dielectric constant layer 14 are formed sufficiently thick compared with the wavelengths of the lights.

As shown in FIG. 21, a steep reduction of reflectance near an incident angle of 23 degrees to plasmon excitation layer 15 is due to coupling with plasmon, because this angle is larger than a full-reflection angle. Thus, according to the Example, there is anisotropy in an angle coupled with plasmon, and its condition is narrow. The longer is the wavelength of the light incident on plasmon excitation layer 15, the steeper is the reduction of reflectance. This indicates that the longer is the wavelength, the higher is the directivity of the light output from the light emitting element. Hereinafter, radiation characteristics of light having a wavelength of 459 nanometers are discussed.

Figure 22:
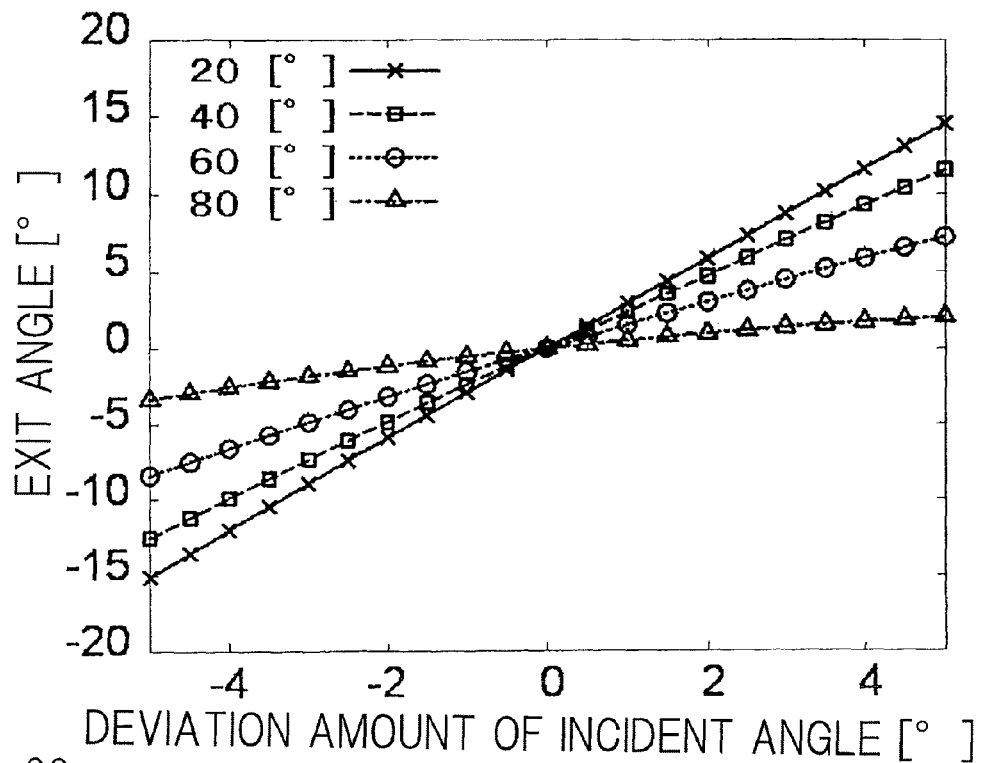
FIG. 22 shows a relationship between a deviation amount of an incident angle of light incident on a photonic crystal of a wave vector conversion layer and an exit angle of light output from the wave vector conversion layer.

FIG. 22 shows changes of exit angles with respect to the deviation amounts of incident angles to the photonic crystal of wave vector conversion layer 17. In FIG. 22, straight lines respectively connecting marks of "x", "□", "o" and "Δ" indicate results of designing grating pitches of the photonic crystal so that lights entered at incident angles of 20°, 40°, 60° and 80° to the photonic crystal can exit from the photonic crystal at an exit angle of 0°. The larger the incident angle to the photonic crystal, the greater can be the suppression of variance on exit angles with respect to variance on incident angles.

Figure 23:
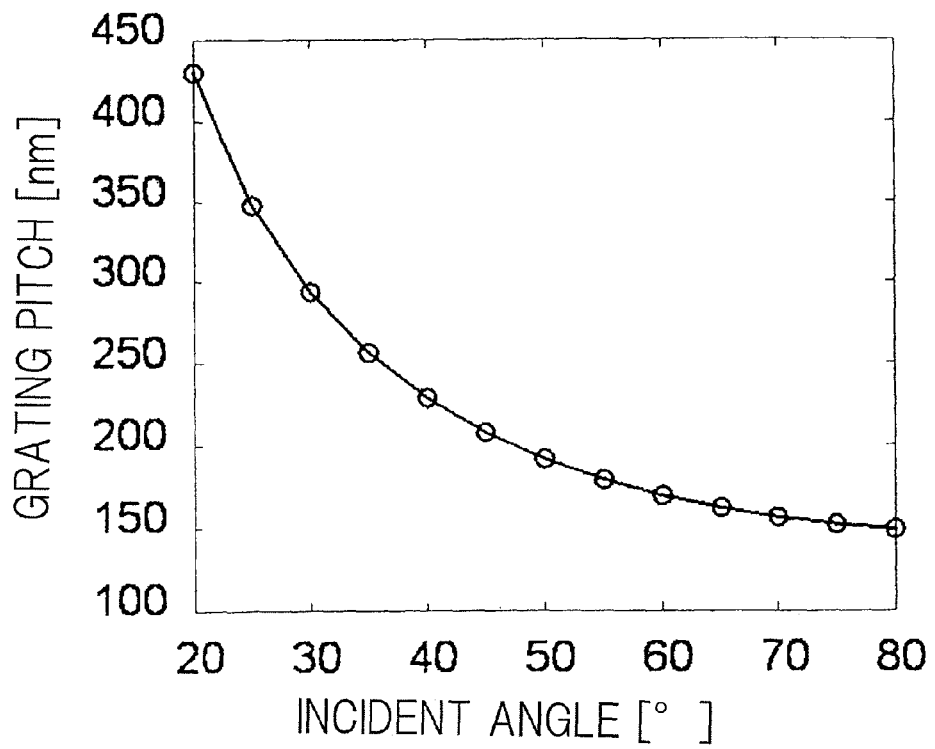
FIG. 23 shows a relationship between the incident angle of the light incident on the photonic crystal of the wave vector conversion layer and a grating pitch to output light from the wave vector conversion layer at an exit angle of 0°.

FIG. 23 shows a change of the grating pitch of the photonic crystal when the incident light is output in the direction of the exit angle of 0° with respect to the incident angle. As shown in FIG. 23, as the incident angle to the photonic crystal increases, the grating pitches of the photonic crystal become narrower.

Figure 24:
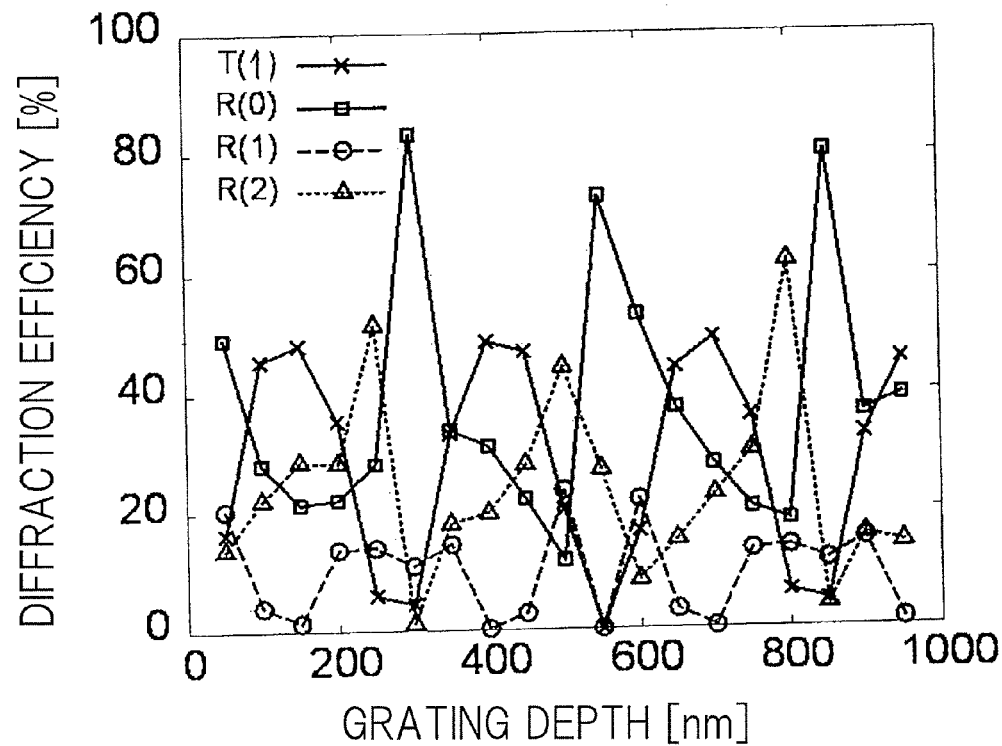
FIG. 24 shows a relationship between a grating depth and diffraction efficiency in the photonic crystal of the wave vector conversion layer.

FIG. 24 shows a relationship between the grating depth of the photonic crystal and diffraction efficiency. In this case, the grating pitch of the photonic crystal is set to 228 nanometers. This is a condition of outputting the light of an incident angle of 40° in the direction of a diffraction angle of 0°. In FIG. 24, straight lines respectively connecting marks of "x", "□", "o" and "Δ" indicate the diffraction intensities of transmitted first-order diffracted light, reflected 0-order diffracted light, reflected first-order diffracted light, and reflected second-order diffracted light by the photonic crystal. As shown in FIG. 24, the diffraction efficiency cyclically changes with respect to the change of the grating depth of the photonic crystal. There is an almost reverse relationship between the change of the diffraction frequency of the transmitted first-order diffracted light and the change of the diffraction frequency of the reflected 0-order diffracted light.

Figure 25:
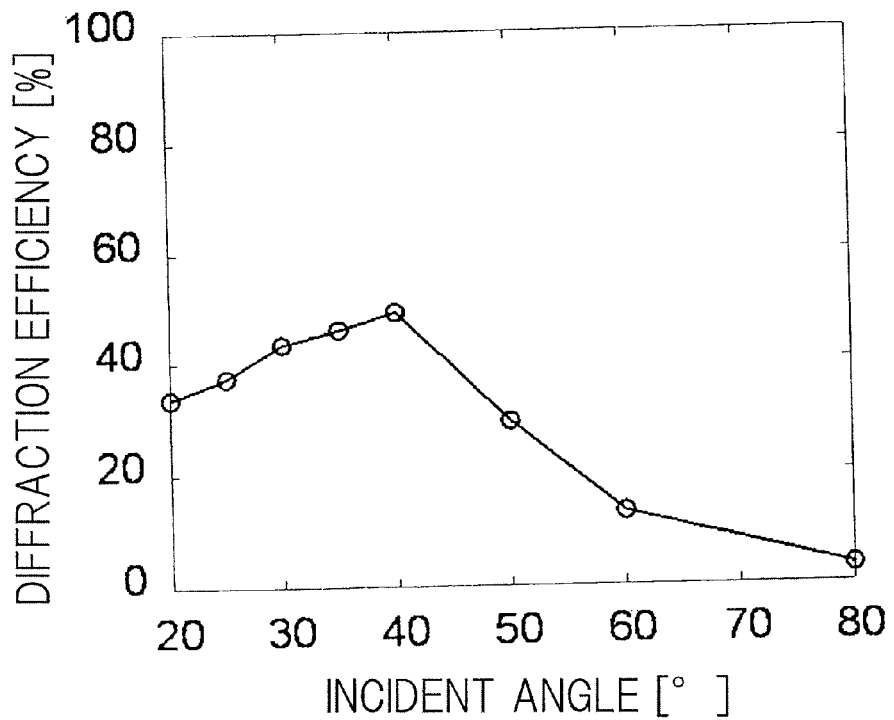
FIG. 25 shows a relationship between an incident angle to the photonic crystal and diffraction efficiency in the photonic crystal of the wave vector conversion layer.

FIG. 25 shows the relationship between an incident angle to the photonic crystal of the wave vector conversion layer and diffraction efficiency. In this case, the diffraction efficiency is maximum diffraction efficiency at a predetermined grating depth where the diffraction of transmitted first-order light becomes maximum when the grating depth of the photonic crystal is changed from 50 nanometers to 950 nanometers. As shown in FIG. 25, the diffraction efficiency of the transmitted first-order light takes a maximum value when light enters the photonic crystal at an incident angle of 40°. In the range before and after the incident angle of 40°, the increase of the incident angle is accompanied by a monotonous increase or a monotonous reduction of the diffraction efficiency of the transmitted first-order light. Thus, an optimal condition is set when the dielectric constants of low dielectric constant layer 14 and high dielectric constant layer 16 are adjusted, and light enters the photonic crystal of wave vector conversion layer 17 near the incident angle of 40°.

Figure 26:
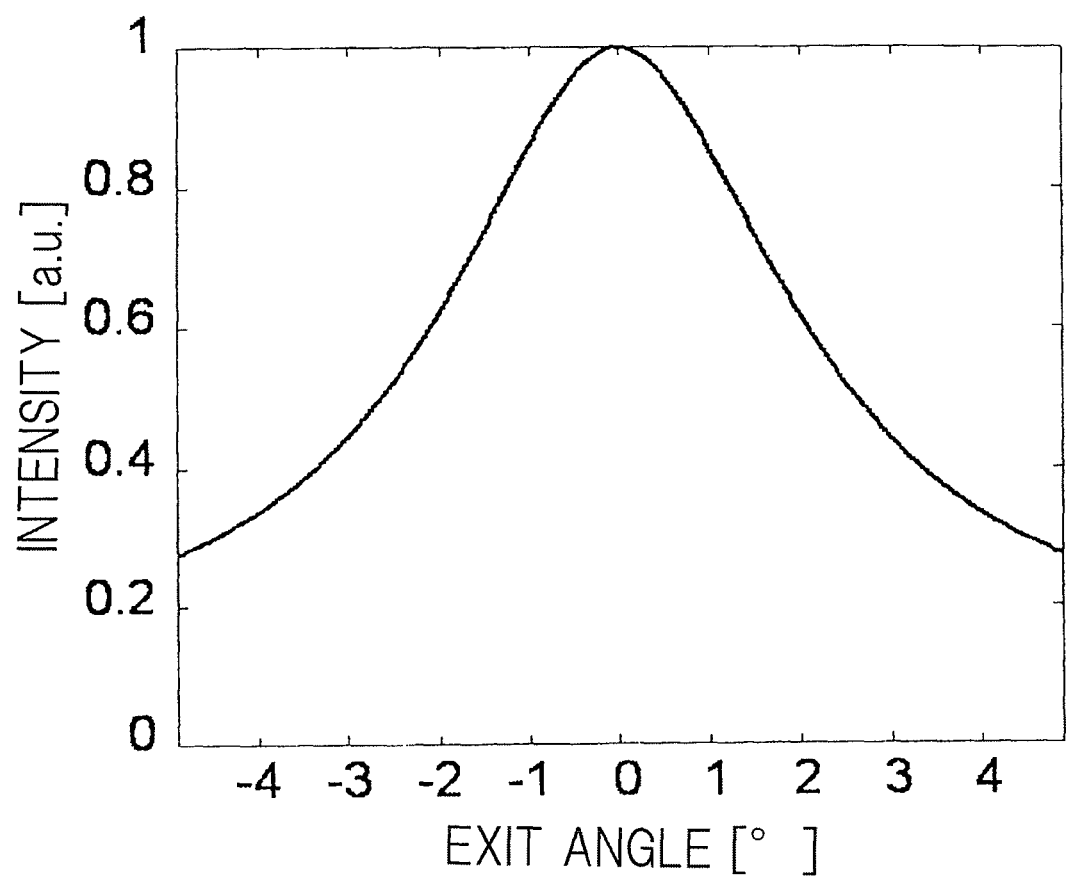
FIG. 26 shows a light distribution of the output light of the light emitting element when light enters into the photonic crystal of the wave vector conversion layer at an incident angle of 40°.

FIG. 26 shows an orientation distribution of the output light of the light emitting element. Specifically, in FIG. 26, a horizontal axis indicates the exit angle of the output light, while a vertical axis indicates the intensity of the output light. As conditions, the grating pitch of the photonic crystal was set to 228 nanometers, and the incident angle of light to the photonic crystal was set to 40°. In this case, when the half-value overall width of the output light was a radiation width, the radiation width of the output light was 5.2°. In other words, a radiation angle was ±2.6°.

As described above, according to the light emitting element of this embodiment, using plasmon excitation layer 15 enables an increase of directivity of the radiation angle of the output light from the light emitting element, and appropriately adjusting the grating structure of wave vector conversion layer 17 enables a further increase of the directivity by narrowing the radiation angle that is equal to or less than ±3°. Further, in the light emitting element of this embodiment, since hole-transport layer 11, active layer 12, and electron-transport layer 13 included in the light source layer can be formed by using the p-type semiconductor layer, the active layer made of an inorganic material, and the inorganic semiconductor as the type semiconductor as in the case of the general LED, the light emitting element of this embodiment can acquire a luminous flux of about several thousand lumina.

Example 2

Figure 27:
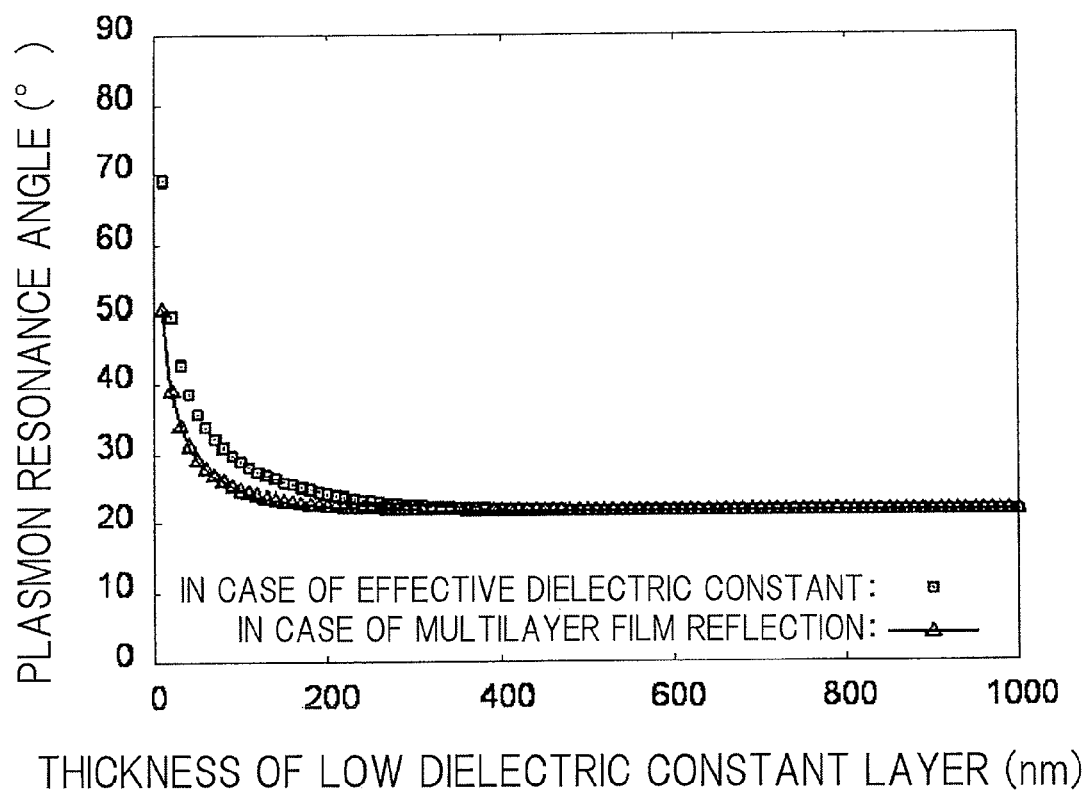
FIG. 27 shows a comparison between a plasmon resonance angle calculated from an effective dielectric constant and a plasmon resonance angle acquired by multiplayer film reflectance calculation in the light emitting element of the first embodiment.

FIG. 27 shows comparison of a plasmon resonance angle (o in the drawing) obtained from an effective dielectric constant calculated by using formula (1) with a plasmon resonance angle (□ in the drawing) obtained from multilayer film reflection calculation in light emitting element 1 according to the first embodiment. In FIG. 26, the horizontal axis indicates the thickness of the low dielectric constant layer, and the vertical axis indicates the plasmon resonance angle. As shown in FIG. 26, the calculated value by an effective dielectric constant and the calculated value by multilayer film reflection match each other, and a condition of plasmon resonance can apparently be defined by the effective dielectric constant defined by formula (1).

$Al_2O_3$ was used for substrate 10, GaN was used for hole-transport layer 11 and electron-transport layer 13, porous $SiO_2$ was used for low dielectric constant layer 14, Ag was used for plasmon excitation layer 15, and $TiO_2$ was used for high dielectric constant layer 16, and thicknesses thereof were respectively set to 0.5 millimeters, 113 nanometers, 10 nanometers, 50 nanometers, and 0.5 millimeters. Calculation was carried out with the emission wavelength of light source layer 4 set to 460 nanometers. The material for wave vector conversion layer 17 was $TiO_2$, and the depth, the pitch, and the duty ratio of the periodic structure were respectively set to 200 nanometers, 221 nanometers, and 0.5.

Figure 28:
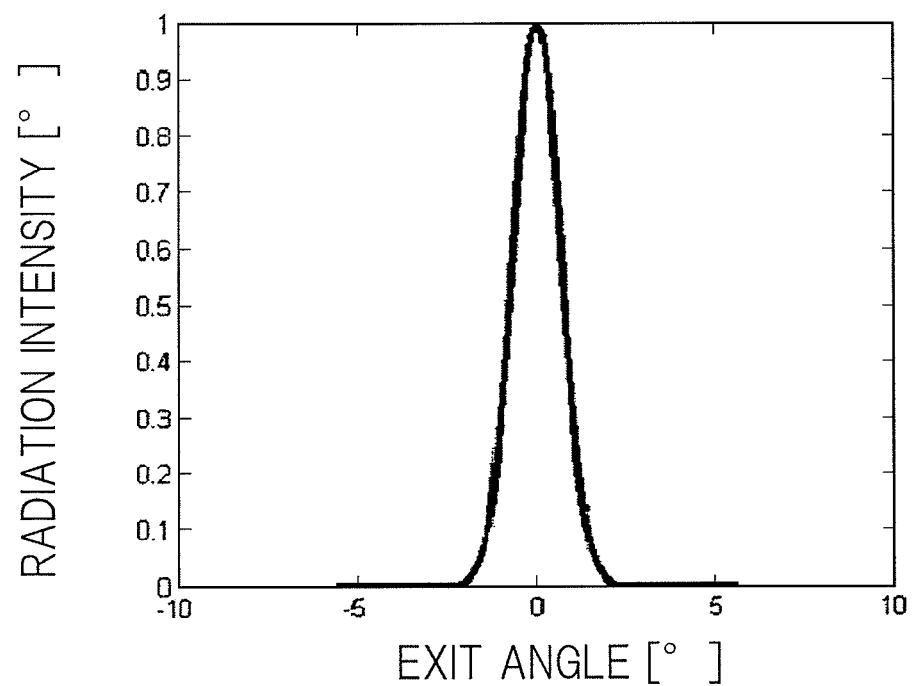
FIG. 28 shows an angle distribution of the output light of the light emitting element of the first embodiment.

FIG. 28 shows angle distribution in the output light of light emitting element 1 according to the first embodiment calculated by adding the abovementioned thickness of each layer. In FIG. 28, the horizontal axis indicates the exit angle of the output light, while the vertical axis indicates intensity of the output light. The output light under these conditions does not have an annular distribution, but has the light distribution of a Gaussian function. However, the pitch is shifted from 250 nanometers to disrupt the peak, thereby acquiring an annular orientation distribution.

For simplicity, calculation was carried out two-dimensionally. When the full width of an angle where intensity of the light output from light emitting element 1 was halved was a radiation angle, the radiation angle was ±0.8 (deg) for each light having a wavelength of 460 nanometers.

Thus, according to light emitting element 1 of the embodiment, directionality of the radiation angle of the output light from light emitting element 1 can be improved, and directionality can be further improved by appropriately adjusting the grating structure of wave vector conversion layer 17 to narrow the radiation angle by ±5 degrees.

According to Example 2, effective dielectric constants of the exit side portion and the incident side portion of plasmon excitation layer 15 are respectively 9.8 and 3.1 by formula (1). Imaginary parts of z-direction wave numbers on the exit side and the incident side of the surface plasmon are respectively 0 and $2.23 \times 10^7 m^{-1}$ by formula (2). Assuming that the effective interaction distance of the surface plasmon is a distance where intensity of the surface plasmon is $e^{-2}$, by $1/Im(k_{spp,z})$, effective interaction distances of the surface plasmon are respectively infinite and 45 nanometers on the exit side and the incident side.

Figure 29:
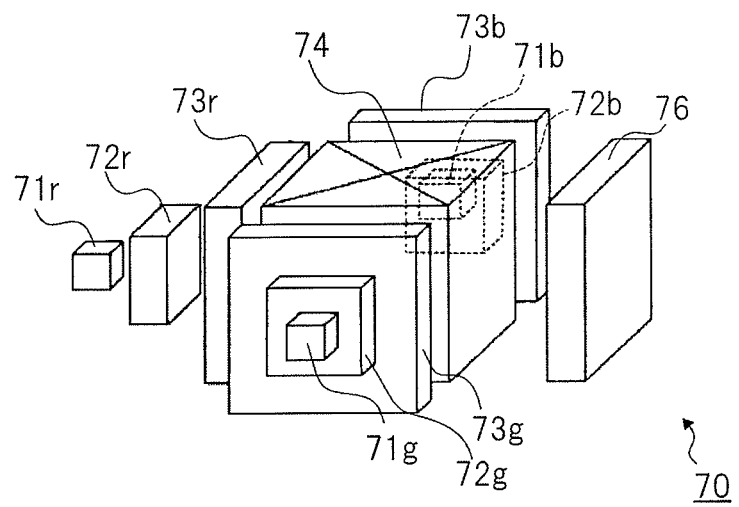
FIG. 29 schematically shows a LED projector to which the light emitting element of the embodiment is applied.

Lastly, a configuration example of a LED projector serving as a projection display device to which the light emitting elements of the first to ninth embodiments are applied is described referring to the drawing. FIG. 29 schematically shows the LED projector of the embodiment.

As shown in FIG. 29, LED projector 70 according to the embodiment includes red (R) light emitting element 71r, green (G) light emitting element 71g, blue (B) light emitting element 71b, illumination optical systems 72r, 72g and 72b into which lights output from light emitting elements 71r, 71g and 71b enter, and light bulbs 73r, 73g and 73b serving as display elements into which the lights passed through illumination optical systems 72r, 72g and 72b enter. LED projector 70 also includes cross dichroic prism 74 for synthesizing R, G and B lights entered after addition of image information by light bulbs 73r, 73g and 73b, and projection optical system 76 that includes a projection lens (not shown) for projecting the output light from cross dichroic prism 74 onto a projection surface such as a screen.

LED projector 70 has a configuration applied to a three-plate projector. Illumination optical systems 72r, 72g and 72b include, for example, rod lenses for making luminance uniform. Light bulbs 73r, 73g and 73b include, for example, liquid crystal display panels or DMDs. Needless to say, the abovementioned light emitting element of the embodiment can be applied to a single-plate projector.

According to LED projector 70 of this embodiment, the application of the abovementioned light emitting element of the embodiment enables improvement of the luminance of a projected image.

In LED projector 70, axially symmetric polarization ½ wavelength plate 50 shown in FIGS. 17, and 18A and 18B is preferably located on the optical path of the output light from light emitting elements 71r, 71g and 71b. This can suppress light loss at light bulbs 73r, 73g and 73b. When the illumination optical system includes a polarizer, axially symmetric polarization ½ wavelength plate 50 is preferably located between the polarizer and light emitting element 71.

The present invention has been described referring to the embodiments. However, the present invention is not limited to the embodiments. Various changes understandable to those skilled in the art can be made to the configuration and the specifics of the present invention within the scope of the invention.

This application claims priority from Japanese Patent Application No. 2009-250282 filed Oct. 30, 2009, which is hereby incorporated by reference herein in its entirety.

The invention claimed is:

1. A light emitting element comprising:
a light source layer; and
an optical element layer stacked on the light source layer, into which light from the light source layer enters, wherein:
the light source layer includes a substrate and a pair of layers, namely, a hole-transport layer and an electron-transport layer, formed on the substrate;
the optical element layer includes a plasmon excitation layer stacked on a side of the light source layer, which is opposite to the substrate side of the light source layer, and which has a plasma frequency higher than a frequency of light output from the light source layer, and an exit layer stacked on the plasmon excitation layer, which converts light incident from the plasmon excitation layer into light having a predetermined exit angle to output the light; and
the plasmon excitation layer is sandwiched between two layers having dielectric properties.

2. The light emitting element according to claim 1, wherein an effective dielectric constant of an incident side portion including a structure stacked on the light source layer side of the plasmon excitation layer is lower than that of an exit side portion including a structure stacked on the exit layer side of the plasmon excitation layer and a medium brought into contact with the exit layer.

3. The light emitting element according to claim 2, wherein:
the effective dielectric constant is determined based on a dielectric constant distribution of dielectrics in the incident side portion or the exit side portion and based on a distribution of a surface plasmon in the direction vertical to the interface of the plasmon excitation layer in the incident side portion or the exit side portion.

4. The light emitting element according to claim 1, further comprising an active layer formed between the hole-transport layer and the electron-transport layer.

5. The light emitting element according to claim 1, further comprising a dielectric constant layer formed adjacently to the exit layer side of the plasmon excitation layer or the light source layer side of the plasmon excitation layer, or formed adjacently to both the exit layer side of the plasmon excitation layer and the light source layer side of the plasmon excitation layer.

6. The light emitting element according to claim 5, wherein:
the plasmon excitation layer is sandwiched between the pair of dielectric constant layers; and
a dielectric constant of the dielectric constant layer adjacent to the light source layer side of the plasmon excitation layer is lower than that of the dielectric constant layer adjacent to the exit layer side of the plasmon excitation layer.

7. The light emitting element according to claim 5, wherein the dielectric constant layer formed adjacently to the light source layer side of the plasmon excitation layer is a low dielectric constant layer having a lower dielectric constant than that of the layer adjacent to the exit layer side of the plasmon excitation layer.

8. The light emitting element according to claim 7, wherein the low dielectric constant layer is formed by stacking a plurality of dielectric layers different in dielectric constant, and the plurality of dielectric layers are arranged so that dielectric constants can be sequentially decreased from the light source layer side to the plasmon excitation layer side.

9. The light emitting element according to claim 7, wherein the low dielectric constant layer has a distribution of dielectric constants that gradually decrease from the light source layer side to the plasmon excitation layer side.

10. The light emitting element according to claim 7, wherein the low dielectric constant layer is a porous layer.

11. The light emitting element according to claim 7, wherein the low dielectric constant layer is conductive.

12. The light emitting element according to claim 5, wherein the dielectric constant layer formed adjacently to the exit layer side of the plasmon excitation layer is a high dielectric constant layer having a higher dielectric constant than that of the layer adjacent to the light source layer side of the plasmon excitation layer.

13. The light emitting element according to claim 12, wherein the high dielectric constant layer is formed by stacking a plurality of dielectric layers different in dielectric constant, and the plurality of dielectric layers are arranged so that dielectric constants can be sequentially decreased from the plasmon excitation layer side to the exit layer side.

14. The light emitting element according to claim 12, wherein the high dielectric constant layer has a distribution of dielectric constants that gradually decrease from the plasmon excitation layer side to the exit layer side.

15. The light emitting element according to claim 1, wherein the hole-transport layer or the electron-transport layer that comprises the pair of layers is formed adjacently to the plasmon excitation layer, and has a lower dielectric constant than that of the layer adjacent to the exit layer side of the plasmon excitation layer.

16. The light emitting element according to claim 1, wherein the exit layer has a surface periodic structure.

17. The light emitting element according to claim 1, wherein the exit layer is made of a photonic crystal.

18. The light emitting element according to claim 1, wherein the plasmon excitation layer is formed by stacking a plurality of metal layers made of different metallic materials.

19. The light emitting element according to claim 1, wherein the plasmon excitation layer is made of a element selected from elements of Ag, Au, Cu, Pt, and Al or an alloy containing at least one of the elements.

20. The light emitting element according to claim 1, wherein in the hole-transport layer or the electron-transport that comprises the pair, a part of a surface orthogonal to a thickness direction is exposed, and an electrode is disposed in the exposed part.

21. The light emitting element according to claim 1, wherein the light source layer further includes an electrode layer disposed between the light source layer and the hole-transport layer or the electron-transport that comprises the pair of layers.

22. The light emitting element according to claim 1, wherein in the plasmon excitation layer, a part of a surface orthogonal to the thickness direction is exposed, and current is supplied to the exposed part.

23. The light emitting element according to claim 1, wherein:
- the light source layer includes a transparent electrode layer stacked on the side opposite the substrate side, and an active layer stacked on the transparent electrode layer, in which electrons and holes are generated by light emitted from between the hole-transport layer and the electron-transport layer; and
- the plasmon excitation layer has a plasma frequency higher than a frequency of light generated when the active layer is excited by the light emitted from between the hole-transport layer and the electron-transport layer.

24. A light source device comprising:
- the light emitting element according to claim 1; and
- a polarizing conversion element that uniformly sets axially symmetric polarized light that enters from the light emitting element in a predetermined polarized state.

25. A projection display device comprising:
- the light emitting element according to claim 1;
- a display element that adds image information to the output light of the light emitting element; and
- a projection optical system that projects a projected image by light output from the display element.

26. A projection display device comprising:
- the light emitting element according to claim 1;
- a display element that adds image information to the output light of the light emitting element;
- a projection optical system that projects a projected image by light output from the display element; and
- a polarizing conversion element stacked on an optical path between the light emitting element and the display element, which uniformly sets axially symmetric polarized light that enters from the light emitting element in a predetermined polarized state.

* * * * *

UNITED STATES PATENT AND TRADEMARK OFFICE
CERTIFICATE OF CORRECTION

PATENT NO. : 9,028,071 B2
APPLICATION NO. : 13/504863
DATED : May 12, 2015
INVENTOR(S) : Masanao Natsumeda et al.

It is certified that error appears in the above-identified patent and that said Letters Patent is hereby corrected as shown below:

In the Specification:

Column 2, Line 21: Delete "Hoepiher," and insert -- Hoepfner, --

Column 7, Line 30: Delete "the" and insert -- of the --

Column 9, Line 19: Delete "$NaIF_6$," and insert -- $NaAlF_6$, --

Signed and Sealed this
Twenty-third Day of August, 2016

Michelle K. Lee
*Director of the United States Patent and Trademark Office*